(12) United States Patent
Kawasaki et al.

(10) Patent No.: US 6,403,779 B1
(45) Date of Patent: Jun. 11, 2002

(54) REGIOSELECTIVE SYNTHESIS OF 2'-O-MODIFIED NUCLEOSIDES

(75) Inventors: Andrew M. Kawasaki, Oceanside; Allister S. Fraser; Muthiah Manoharan, both of Carlsbad; P. Dan Cook, Lake San Marcos; Thazha P. Prakash, Carlsbad, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/227,782

(22) Filed: Jan. 8, 1999

(51) Int. Cl.$^7$ .......................... C07H 21/02; C07H 19/00

(52) U.S. Cl. .................. 536/23.1; 536/27.1; 536/24.3; 536/24.5; 536/25.3; 536/27.21; 536/28.1

(58) Field of Search ............................ 536/23.1, 24.3, 536/24.5, 24.31, 25.1, 25.3, 27.1, 27.21, 28.1

(56) References Cited

U.S. PATENT DOCUMENTS

| | | | |
|---|---|---|---|
| 5,138,045 A | 8/1992 | Cook et al. | 536/27 |
| 5,218,105 A | 6/1993 | Cook et al. | 536/25.31 |
| 5,223,618 A | 6/1993 | Cook et al. | 544/276 |
| 5,359,044 A | 10/1994 | Cook et al. | 536/23.1 |
| 5,378,825 A | 1/1995 | Cook et al. | 536/25.34 |
| 5,386,023 A | 1/1995 | Sanghvi et al. | 536/25.3 |
| 5,457,191 A | 10/1995 | Cook et al. | 536/27.13 |
| 5,459,255 A | 10/1995 | Cook et al. | 536/27.13 |
| 5,466,786 A | 11/1995 | Buhr et al. | 536/26.26 |
| 5,489,677 A | 2/1996 | Sanghvi et al. | 536/22.1 |
| 5,506,351 A | 4/1996 | McGee | 536/55.3 |
| 5,541,307 A | 7/1996 | Cook et al. | 536/23.1 |
| 5,543,507 A | 8/1996 | Cook et al. | 536/23.1 |
| 5,571,902 A | 11/1996 | Ravikumar et al. | 536/22.1 |
| 5,578,718 A | 11/1996 | Cook et al. | 536/27.21 |
| 5,587,361 A | 12/1996 | Cook et al. | 514/44 |
| 5,587,469 A | 12/1996 | Cook et al. | 536/23.1 |

FOREIGN PATENT DOCUMENTS

| | | |
|---|---|---|
| WO | WO 91/06556 | 5/1991 |
| WO | WO 91/10671 | 7/1991 |
| WO | WO 92/02258 | 2/1992 |
| WO | WO 92/03568 | 3/1992 |
| WO | WO 93/07883 | 4/1993 |
| WO | WO 94/02501 | 2/1994 |
| WO | 94/02501 | * 2/1994 |
| WO | WO 98/35978 | 8/1998 |

OTHER PUBLICATIONS

Manoharan et al., Tetrahedron Letters, vol. 32(49), pp. 7171–7174, 1991.*
Kawasaki et al., Intl. Round Table, Nucleosides, Nucleotides . . . , pp. 1–16, Sep. 1998.*
Baldwin et al., "Reductive Deoxygenation of Esters with Trichlorosilane", *J. Org. Chem.*, 1975, 40(26), 3885–3887.

Beaucage, S.L. et al., "Deoxynucleoside Phosphoramidites–A New Class of Key Intermediates for Deoxypolynucleotide Synthesis", *Tetrahedron Letts.*, 1981, 22, 1859–1862.

Carey, F.A. et al., *Advanced Organic Chemistry, Part A: Structures and Mechanisms*, 3rd Edition, Plenum Press, New York, NY, 1990, 296–297.

Caruthers, M.H., "Synthesis of Oligonucleotides and Oligonucleotide Analogues", *Oligonucleotides: Antisense Inhibitors of Gene Expression*, 1989, Chapter 1, Cohen, J.S. (Ed.), CRC Press, Boca Raton, FL, 7–24.

Cook, P.D., "Second Generation Antisense Oligonucleotides: 2'–Modifications", Bristol, J.A. (ed.), *Annu. Rep. Med. Chem.* Academic Press, New York, 1998, 33, 313–325.

Guschlbauer et al., "Nucleoside conformation is determined by the electronegativity of the sugar substituent", *Nucl. Acids Res.*, 1980, 8(6), 1421–1433.

Hobbs, J. et al., "Polynucleotides Containing 2'–Chloro–2'–deoxyribose", *Biochem.*, 1972, 11, 4336–4344.

Ikehara, M. et al., "Polynucleotides. LVI. Synthesis and properties of poly(2'–deoxy–2'–fluroadenylic acid)", *Nucl. Acids Res.*, 1978, 5, 3315–3325.

Ikehara, M. et al., "Polynucleotides. L. Synthesis and properties of poly(2'–chloro–2'–deoxyadenylic acid) and poly(2'–bromo–2'–deoxyadenylic acid)", *Nucl. Acids Res.*, 1977, 4, 4249–4260.

Inoue, H. et al., "Synthesis and hybridization studies on two complemetary nona(2'–O–methyl)ribonucleotides", *Nucl. Acids Res.*, 1987, 15 6131–6148.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Kawasaki et al., "Synthesis, Hybridization, and Nuclease Resistance Properties of 2'–O–Aminooxyethyl Modified Oligonucleotides", Gosselin, G. et al. (eds.), *XIII International Round Table, Nucleosides, Nucleotides, and their Biological Applications*, Montpellier, France, Sep. 6–10, 1998, 16 pages.

Keller, T.H. et al., "A General Method for the Synthesis of 2'–O–Modified Ribonucleosides", *Helvetica Chimica Acta*, 1993, 76, 884–892.

(List continued on next page.)

Primary Examiner—James O. Wilson
Assistant Examiner—Howard V. Owens, Jr.
(74) Attorney, Agent, or Firm—Woodcock Washburn LLP

(57) ABSTRACT

Methods for the regioselective alkylation at the 2'-hydroxy position over the 3'-hydroxy position of nucleosides and nucleoside analogs, forming 2'-O-ester modified compounds, are disclosed. Reduction and derivatization of the 2'-O-ester provides 2'-O-modified nucleosides and nucleoside analogs useful for the synthesis of oligomeric compounds having improved hybridization affinity and nuclease resistance.

9 Claims, No Drawings

OTHER PUBLICATIONS

Manoharan, M. et al., "Novel Functionalization of the Sugar Moiety of Nucleic Acids for Multiple Labeling in the Minor Groove", *Tetrahedron Letts.,* 1991, 32, 7171–7174.

March, J., *Advanced Organic Chemistry,* 4th Edition, Wiley Interscience, New York, 1992, 386–387.

Monia, B.P. et al., "Evaluation of 2'–Modified Oligonucleotides Containing 2'–Deoxy Gaps as Antisense Inhibitors of Gene Expression", *J. Biol. Chem.,* 1993, 268, 14514–14522.

Ohtsuka et al., "Recognition by restriction endonuclease EcoRI of deoxyoctanucleotides containing modified sugar moieties", *European J. Biochem.,* 1984, 139, 447–450.

Peoc'h et al., "Synthesis and Evaluation of 2'–Modified MMI Linked Dimers in Antisense Constructs", *Nucleosides Nucleotides,* 1997, 16(7–9), 959–962.

Secrist, J.A. et al., "Synthesis and Biological Activity of 4'–Thionucleosides", 10th International Roundtable: Nucleosides, Nucleotides and their Biological Applications, Sep. 16–20 1992, Abstract 21, Park City, Utah, 40.

Shibahara, S. et al., "Inhibition of human immunodeficiency virus (HIV–1) replication by synthetic oligo–RNA derivatives", *Nucl. Acids Res.,* 1989, 17, 239–252.

Takaku, H. et al., "Synthesis of Oligoribonucleotides Using 4–Methoxybenzyl Group as a New Protecting Group of the 2'–Hydroxyl Group of Adenosine", *Chem. Letts.,* 1982, 189–192.

Walker et al., "Analysis of Hydroxylamine Glycosidic Linages: Structural Consequences of the NO Bond in Calicheamicin", *J. Am. Chem.,* 1994, 116, 3197–3206.

* cited by examiner

SEQUENCE LISTING

<160> NUMBER OF SEQ ID NOS: 28

<210> SEQ ID NO 1
<211> LENGTH: 19
<212> TYPE: DNA
<213> ORGANISM: Artificial Sequence
<220> FEATURE:
<221> NAME/KEY: misc_feature
<222> LOCATION: (15)..(18)
<223> OTHER INFORMATION: 5-methyl- 2'- aminooxy ethoxy
<223> OTHER INFORMATION: Description of Artificial  Sequence: Novel
      Sequence

<400> SEQUENCE: 1
tttttttttt tttttttt                                                       19

<210> SEQ ID NO 2
<211> LENGTH: 19
<212> TYPE: DNA
<213> ORGANISM: Artificial Sequence
<220> FEATURE:
<221> NAME/KEY: misc_feature
<222> LOCATION: (15)..(18)
<223> OTHER INFORMATION: 5- methyl- 2'- dime thylaminooxyethoxy
<223> OTHER INFORMATION: Description of Artificial  Sequence: Novel
      Sequence

<400> SEQUENCE: 2
tttttttttt tttttttt                                                       19

<210> SEQ ID NO 3
<211> LENGTH: 19
<212> TYPE: DNA
<213> ORGANISM: Artificial Sequence
<220> FEATURE:
<221> NAME/KEY: misc_feature
<222> LOCATION: (15)..(18)
<223> OTHER INFORMATION: 2'-methoxyethoxy
<223> OTHER INFORMATION: Description of Artificial  Sequence: Novel
      Sequence

<400> SEQUENCE: 3
tttttttttt tttttttt                                                       19

<210> SEQ ID NO 4
<211> LENGTH: 19
<212> TYPE: DNA
<213> ORGANISM: Artificial Sequence
<220> FEATURE:
<221> NAME/KEY: misc_feature
<222> LOCATION: (16)..(19)
<223> OTHER INFORMATION: 5- methyl- 2'- dime thylaminooxyethoxy
<223> OTHER INFORMATION: Description of Artificial  Sequence: Novel
      Sequence

<400> SEQUENCE: 4
tttttttttt tttttttt                                                       19

<210> SEQ ID NO 5
<211> LENGTH: 19
<212> TYPE: DNA
<213> ORGANISM: Artificial Sequence
<220> FEATURE:
<221> NAME/KEY: misc_feature
<222> LOCATION: (16)..(19)
<223> OTHER INFORMATION: 5- methyl- 2'-methoxye thoxy
<223> OTHER INFORMATION: Description of Artificial  Sequence: Novel
      Sequence

```
<400> SEQUENCE: 5
tttttttttt tttttttt                                              19

<210> SEQ ID NO 6
<211> LENGTH: 19
<212> TYPE: DNA
<213> ORGANISM: Artificial Sequence
<220> FEATURE:
<221> NAME/KEY: misc_feature
<222> LOCATION: (16)..(19)
<223> OTHER INFORMATION: 5- methyl- 2'-O-propyl
<223> OTHER INFORMATION: Description of Artificial  Sequence: Novel
      Sequence

<400> SEQUENCE: 6
tttttttttt tttttttt                                              19

<210> SEQ ID NO 7
<211> LENGTH: 19
<212> TYPE: DNA
<213> ORGANISM: Artificial Sequence
<220> FEATURE:
<221> NAME/KEY: misc_feature
<222> LOCATION: (18)
<223> OTHER INFORMATION: 5- methyl- 2'- dime thylaminooxyethoxy
<223> OTHER INFORMATION: Description of Artificial  Sequence: Novel
      Sequence

<400> SEQUENCE: 7
tttttttttt tttttttt                                              19

<210> SEQ ID NO 8
<211> LENGTH: 19
<212> TYPE: DNA
<213> ORGANISM: Artificial Sequence
<220> FEATURE:
<221> NAME/KEY: misc_feature
<222> LOCATION: (18)
<223> OTHER INFORMATION: 5- methyl- 2'-methoxye thoxy
<223> OTHER INFORMATION: Description of Artificial  Sequence: Novel
      Sequence

<400> SEQUENCE: 8
tttttttttt tttttttt                                              19

<210> SEQ ID NO 9
<211> LENGTH: 18
<212> TYPE: DNA
<213> ORGANISM: Artificial Sequence
<220> FEATURE:
<221> NAME/KEY: misc_feature
<222> LOCATION: (9)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 9
ctcgtacctt tccggtcc                                              18

<210> SEQ ID NO 10
<211> LENGTH: 16
<212> TYPE: DNA
<213> ORGANISM: Artificial Sequence
<220> FEATURE:
<221> NAME/KEY: misc_feature
<222> LOCATION: (1)
<223> OTHER INFORMATION: 5-methyl-2'-dimethylaminooxy ethoxy
<221> NAME/KEY: misc_feature
```

```
<222> LOCATION: (7)
<223> OTHER INFORMATION: 5-methyl-2'-dimethylaminooxy ethoxy
<221> NAME/KEY: misc_feature
<222> LOCATION: (9)
<223> OTHER INFORMATION: 5-methyl-2'-dimethylaminooxy ethoxy
<221> NAME/KEY: misc_feature
<222> LOCATION: (15)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 10
tccaggtgtc cgcatc                                                  16

<210> SEQ ID NO 11
<211> LENGTH: 16
<212> TYPE: DNA
<213> ORGANISM: Artificial Sequence
<220> FEATURE:
<221> NAME/KEY: misc_feature
<222> LOCATION: (4)..(13)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 11
gcgttttttt tttgcg                                                  16

<210> SEQ ID NO 12
<211> LENGTH: 19
<212> TYPE: DNA
<213> ORGANISM: Artificial Sequence
<220> FEATURE:
<221> NAME/KEY: misc_feature
<222> LOCATION: (15)..(18)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 12
tttttttttt ttttttttt                                               19

<210> SEQ ID NO 13
<211> LENGTH: 4
<212> TYPE: DNA
<213> ORGANISM: Artificial Sequence
<220> FEATURE:
<221> NAME/KEY: misc_feature
<222> LOCATION: (1)..(4)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 13 tttt                                                                4

<210> SEQ ID NO 14
<211> LENGTH: 19
<212> TYPE: DNA
<213> ORGANISM: Artificial Sequence
<220> FEATURE:
<221> NAME/KEY: misc_feature
<222> LOCATION: (16)..(19)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 14
tttttttttt ttttttt                                                 19
```

```
<210> SEQ ID NO 15
<211> LENGTH: 19
<212> TYPE: DNA
<213> ORGANISM: Artificial Sequence
<220> FEATURE:
<221> NAME/KEY: misc_feature
<222> LOCATION: (16)..(19)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 15
tttttttttt tttttttt                                                   19

<210> SEQ ID NO 16
<211> LENGTH: 2
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 16 tt                                                                     2

<210> SEQ ID NO 17
<211> LENGTH: 18
<212> TYPE: DNA
<213> ORGANISM: Artificial Sequence
<220> FEATURE:
<221> NAME/KEY: misc_feature
<222> LOCATION: (9)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 17
ctcgtaccat tccggtcc                                                   18

<210> SEQ ID NO 18
<211> LENGTH: 17
<212> TYPE: DNA
<213> ORGANISM: Artificial Sequence
<220> FEATURE:
<221> NAME/KEY: misc_feature
<222> LOCATION: (3)
<223> OTHER INFORMATION: 5-methyl-2'-dimethylaminooxy ethoxy
<221> NAME/KEY: misc_feature
<222> LOCATION: (8)..(9)
<223> OTHER INFORMATION: 5-methyl-2'-dimethylaminooxy ethoxy
<221> NAME/KEY: misc_feature
<222> LOCATION: (13)
<223> OTHER INFORMATION: 5-methyl-2'-dimethylaminooxy ethoxy
<221> NAME/KEY: misc_feature
<222> LOCATION: (16)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 18
ggaccggaag gtacgag                                                    17

<210> SEQ ID NO 19
<211> LENGTH: 24
<212> TYPE: DNA
<213> ORGANISM: Artificial Sequence
<220> FEATURE:
```

```
<221> NAME/KEY: misc_feature
<222> LOCATION: (1)
<223> OTHER INFORMATION: 5-methyl-2'-dimethylaminooxy ethoxy
<221> NAME/KEY: misc_feature
<222> LOCATION: (5)
<223> OTHER INFORMATION: 5-methyl-2'-dimethylaminooxy ethoxy
<221> NAME/KEY: misc_feature
<222> LOCATION: (8)
<223> OTHER INFORMATION: 5-methyl-2'-dimethylaminooxy ethoxy
<221> NAME/KEY: misc_feature
<222> LOCATION: (11)
<223> OTHER INFORMATION: 5-methyl-2'-dimethylaminooxy ethoxy
<221> NAME/KEY: misc_feature
<222> LOCATION: (14)
<223> OTHER INFORMATION: 5-methyl-2'-dimethylaminooxy ethoxy
<221> NAME/KEY: misc_feature
<222> LOCATION: (21)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 19
accgaggagg atcatgtcgt acgc                                              24

<210> SEQ ID NO 20
<211> LENGTH: 18
<212> TYPE: DNA
<213> ORGANISM: Artificial Sequence
<220> FEATURE:
<221> NAME/KEY: misc_feature
<222> LOCATION: (9)
<223> OTHER INFORMATION: 2'-methyleneiminooxyethoxy
<223> OTHER INFORMATION: Description of Artificial  Sequence: Novel
      Sequence

<400> SEQUENCE: 20
ctcgtaccat tccggtcc                                                     18

<210> SEQ ID NO 21
<211> LENGTH: 21
<212> TYPE: DNA
<213> ORGANISM: Artificial Sequence
<220> FEATURE:
<221> NAME/KEY: misc_feature
<222> LOCATION: (1)
<223> OTHER INFORMATION: 2'-methyleneiminooxyethoxy
<221> NAME/KEY: misc_feature
<222> LOCATION: (5)
<223> OTHER INFORMATION: 2'-methyleneiminooxyethoxy
<221> NAME/KEY: misc_feature
<222> LOCATION: (8)
<223> OTHER INFORMATION: 2'-methyleneiminooxyethoxy
<221> NAME/KEY: misc_feature
<222> LOCATION: (11)
<223> OTHER INFORMATION: 2'-methyleneiminooxyethoxy
<221> NAME/KEY: misc_feature
<222> LOCATION: (18)
<223> OTHER INFORMATION: 2'-methyleneiminooxyethoxy
<223> OTHER INFORMATION: Description of Artificial  Sequence: Novel
      Sequence

<400> SEQUENCE: 21
accgaggatc atgtcgtacg c                                                 21

<210> SEQ ID NO 22
<211> LENGTH: 17
<212> TYPE: DNA
<213> ORGANISM: Artificial Sequence
<220> FEATURE:
<221> NAME/KEY: misc_feature
<222> LOCATION: (3)
<223> OTHER INFORMATION: 2'-methyleneiminooxyethoxy
<221> NAME/KEY: misc_feature
```

```
<222> LOCATION: (8)..(9)
<223> OTHER INFORMATION: 2'-methyleneiminooxyethoxy
<221> NAME/KEY: misc_feature
<222> LOCATION: (13)
<223> OTHER INFORMATION: 2'-methyleneiminooxyethoxy
<221> NAME/KEY: misc_feature
<222> LOCATION: (16)
<223> OTHER INFORMATION: 2'-methyleneiminooxyethoxy
<223> OTHER INFORMATION: Description of Artificial  Sequence: Novel
      Sequence

<400> SEQUENCE: 22
ggaccggaag gtacgag                                                    17

<210> SEQ ID NO 23
<211> LENGTH: 18
<212> TYPE: DNA
<213> ORGANISM: Artificial Sequence
<220> FEATURE:
<221> NAME/KEY: misc_feature
<222> LOCATION: (9)
<223> OTHER INFORMATION: 2'-methyleneiminooxyethoxy
<223> OTHER INFORMATION: Description of Artificial  Sequence: Novel
      Sequence

<400> SEQUENCE: 23 ctcgtaccttt tccggtcc                                                  18

<210> SEQ ID NO 24
<211> LENGTH: 16
<212> TYPE: DNA
<213> ORGANISM: Artificial Sequence
<220> FEATURE:
<221> NAME/KEY: misc_feature
<222> LOCATION: (1)
<223> OTHER INFORMATION: 2'-methyleneiminooxyethoxy
<221> NAME/KEY: misc_feature
<222> LOCATION: (7)
<223> OTHER INFORMATION: 2'-methyleneiminooxyethoxy
<221> NAME/KEY: misc_feature
<222> LOCATION: (9)
<223> OTHER INFORMATION: 2'-methyleneiminooxyethoxy
<221> NAME/KEY: misc_feature
<222> LOCATION: (15)
<223> OTHER INFORMATION: 2'-methyleneiminooxyethoxy
<223> OTHER INFORMATION: Description of Artificial  Sequence: Novel
      Sequence

<400> SEQUENCE: 24
tccaggtgtc cgcatc                                                     16

<210> SEQ ID NO 25
<211> LENGTH: 19
<212> TYPE: DNA
<213> ORGANISM: Artificial Sequence
<220> FEATURE:
<221> NAME/KEY: misc_feature
<222> LOCATION: (15)..(18)
<223> OTHER INFORMATION: 2'-methyleneiminooxyethoxy
<223> OTHER INFORMATION: Description of Artificial  Sequence: Novel
      Sequence

<400> SEQUENCE: 25
tttttttttt tttttttt                                                   19

<210> SEQ ID NO 26
<211> LENGTH: 18
<212> TYPE: DNA
<213> ORGANISM: Artificial Sequence
<220> FEATURE:
<221> NAME/KEY: misc_feature
```

```
<222> LOCATION: (9)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 26
ctcgtacctt tccggtcc                                                         18

<210> SEQ ID NO 27
<211> LENGTH: 16
<212> TYPE: DNA
<213> ORGANISM: Artificial Sequence
<220> FEATURE:
<221> NAME/KEY: misc_feature
<222> LOCATION: (1)
<223> OTHER INFORMATION: 5-methyl-2'-dimethylaminooxy ethoxy
<221> NAME/KEY: misc_feature
<222> LOCATION: (7)
<223> OTHER INFORMATION: 5-methyl-2'-dimethylaminooxy ethoxy
<221> NAME/KEY: misc_feature
<222> LOCATION: (9)
<223> OTHER INFORMATION: 5-methyl-2'-dimethylaminooxy ethoxy
<221> NAME/KEY: misc_feature
<222> LOCATION: (15)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 27
tccaggtgtc cgcatc                                                           16

<210> SEQ ID NO 28
<211> LENGTH: 16
<212> TYPE: DNA
<213> ORGANISM: Artificial Sequence
<220> FEATURE:
<221> NAME/KEY: misc_feature
<222> LOCATION: (4)..(13)
<223> OTHER INFORMATION: 5-methyl-2'-dimethylaminooxy ethoxy
<223> OTHER INFORMATION: Description of Artificial  Sequence: Novel
      Sequence

<400> SEQUENCE: 28 gcgtttttttt tttgcg                                                          16
```

REGIOSELECTIVE SYNTHESIS OF 2'-O-MODIFIED NUCLEOSIDES

FIELD OF THE INVENTION

This invention is directed to methods of regioselective alkylation of pentosyl sugar moieties at the 2'-OH position. The present invention is further directed to reduction and derivatization of the 2'-O-alkylated compounds produced by these methods. The methods are useful for the preparation of 2'-O-alkyl nucleotides, nucleosides and nucleoside surrogates that are useful as precursors for the preparation of oligomeric compounds. Such oligomeric compounds are useful as therapeutics, diagnostics, and research reagents.

In certain embodiments of the invention, the inclusion of one or more 2'-O-aminooxyethyl moieties in an oligonucleotide provides, inter alia, improved binding of the oligonucleotide to a complementary strand. In further embodiments of the invention, the inclusion of one or more 2'-O-aminooxyethyl moieties in an oligomeric compound of the invention provides one or more conjugation sites useful for the conjugation of various useful ligands. Such ligands include, for example, reporter groups and groups for modifying uptake, distribution or other pharmacodynamic properties. The specific objectives and advantages of the present invention will become apparent to the art-skilled from the description of the preferred embodiments of the invention.

BACKGROUND OF THE INVENTION

It has been recognized that oligonucleotides and oligonucleotide analogs (oligomeric compounds) can be used to modulate mRNA expression by a mechanism that involves the complementary hybridization of relatively short oligonucleotides to mRNA such that the normal and essential functions of these intracellular nucleic acids are disrupted. Hybridization is the sequence-specific base pair hydrogen bonding of an oligonucleotide to a complementary RNA or DNA.

Oligonucleotides are used as diagnostics, therapeutics and as research reagents. For this, the ability of an oligonucleotide to bind to a specific DNA or RNA with fidelity is an important factor. The relative ability of an oligonucleotide to bind to complementary nucleic acids is compared by determining the melting temperature of a particular hybridization complex. The melting temperature ($T_m$), a characteristic physical property of double helices, is the temperature (in ° C.) at which 50% helical versus coil (unhybridized) forms are present. $T_m$ is measured by using UV spectroscopy to determine the formation and breakdown (melting) of hybridization. Base stacking, which occurs during hybridization, is accompanied by a reduction in UV absorption (hypochromicity). Consequently, a reduction in UV absorption indicates a higher $T_m$. The higher the $T_m$, the greater the strength of the binding of the nucleic acid strands. Therefore, oligonucleotides modified to hybridize with appropriate strength and fidelity to targeted RNA (or DNA) are greatly desired for use as research reagents, diagnostic agents, and as oligonucleotide therapeutics.

Various modifications to the base, sugar and internucleoside linkage have been introduced into oligonucleotides at selected positions, and the resultant effect relative to the unmodified oligonucleotide compared. A number of modifications have been shown to improve one or more aspects of the oligonucleotide. Useful 2'-modifications that have been shown to improve aspects of oligonucleotides include halo, alkoxy and allyloxy groups. Many 2'-O-modified oligonucleotides having increased hybridization and nuclease resistance have been used in antisense research.

The use of antisense compounds as drug candidates with potential clinical applications requires that they form stable duplexes with target mRNA's, prevent translation of messages (most often via RNase H-mediated cleavage), and have resistance to nucleases. Phosphorothioate backbone modified oligonucleotides having 2'-O-modified monomers at selected positions have been reported to be effective antisense molecules. Cook, P. D., 1998, Second Generation 2'-Modified Antisense Oligonucleotides, J. A. Bristol (Ed.), *Annu. Rep. Med. Chem.*, Vol. 33, pp. 313–325, Academic Press, New York. The phosphorothioate internucleoside linkage enhances nuclease resistance, while the 2'-O-modification increases hybridization. Superior antisense activity has been shown for 2'-O-modified oligomeric compounds. Martin, *Helv. Chim. Acta.*, 1995, 78, 486–504. These oligonucleotides were prepared using "gapmer" technology. Monia et al., *J. Biol. Chem.*, 1993, 268, 14514–14522. Gapmer technology utilizes nuclease-resistant internucleoside linkages at selected positions while using native or other internucleoside linkages at internal positions. Generally, the 3' and 5' regions of the oligomeric compound will have contiguous internucleoside linkages providing superior nuclease resistance while the internal region may have native or other internucleoside linkages.

In addition to 2'-O-methoxyethyl modified oligomeric compounds, oligomeric compounds having pseudoisosteres of 2'-O-methoxyethyl modification have also shown superior hybridization qualities. Included in this group of 2'-O-modifications is the 2'-O-aminooxyethyl (AOE) modification. Kawasaki et al., 1998, Synthesis, Hybridization, and Nuclease Resistance Properties of 2'-O-Aminooxyethyl Modified Oligonucleotides, G. Gosselin and B. Rayner (Eds.), *XIII International Round Table, Nucleosides, Nucleotides, and their Biological Applications*, Montpellier, France. The hydroxylamino function present in this modification is observed in nature in the form of glycosylated antibiotics. Walker et al., *J. Am. Chem.*, 1994, 116, 3197–3206. The hydroxylamino function has also been synthetically incorporated into oligonucleotide backbones. Peoc'h et al., *Nucleosides Nucleotides*, 1997, 16, 959–962. Among the unique properties of the hydroxylamino function are the unusual conformational preferences of the N—O bond and the surprisingly low $pK_a$ (MeONH$_2$, 4.2, MeONHMe, 4.75, MeONHMe$_2$, 3.65).

Ikehara et al. (*European J. Biochem.*, 1984, 139, 447) have reported the synthesis of a mixed octamer containing one 2'-deoxy-2'-fluoroguanosine residue or one 2'-deoxy-2'-fluoroadenine residue. Guschlbauer and Jankowski (*Nucleic Acids Res*, 1980, 8, 1421) have shown that the contribution of the C3'-endo conformer increases with increasing electronegativity of the 2'-substituent. Thus, 2'-deoxy-2'-fluorouridine contains 85% of the C3'-endo conformer.

Furthermore, evidence has been presented which indicates that 2'-substituted-2'-deoxyadenosine polynucleotides resemble double-stranded RNA rather than DNA. Ikehara et al. (*Nucleic Acids Res.*, 1978, 5, 3315) have shown that a 2'-fluoro substituent in poly A, poly I, or poly C duplexed to its complement is significantly more stable than the ribonucleotide or deoxyribonucleotide poly duplex as determined by standard melting assays. Ikehara et al. (*Nucleic Acids Res.*, 1978, 4, 4249) have shown that a 2'-chloro or -bromo substituent in poly(2'-deoxyadenylic acid) provides nuclease resistance. Eckstein et al. (*Biochemistry*, 1972, 11, 4336) have reported that poly-(2'-chloro-2'-deoxy-uridylic acid) and poly(2'-chloro-2'-deoxycytidylic acid) are resistant to various nucleases. Inoue et al. (*Nucleic Acids Res.*, 1987, 15, 6131) have described the synthesis of mixed oligonucleotide sequences containing 2'-OMe substituents on every nucleotide. The mixed 2'-OMe-substituted oligonucleotide hybridized to its RNA complement as strongly as the RNA-RNA duplex which is significantly stronger than the same sequence RNA-DNA hetero duplex ($T_m$s, 49.0 and 50.1 versus 33.0 degrees for nonamers) Shibahara et al. (*Nucleic Acids Res.*, 1987, 17, 239) have reported the synthesis of mixed oligonucleotides containing 2'-OMe substituents on every nucleotide. The mixed 2'-OMe-substituted oligonucleotides were designed to inhibit HIV replication.

It is believed that the composite of the hydroxyl group's steric effect, its hydrogen bonding capabilities, and its electronegativity versus the properties of the hydrogen atom is responsible for the gross structural difference between RNA and DNA. Thermal melting studies indicate that the order of duplex stability (hybridization) of 2'-methoxy oligonucleotides is in the order of RNA-RNA>RNA-DNA>DNA-DNA.

International Publication Number WO 91/06556, published May 16, 1991, and U.S. Pat. No. 5,466,786 disclose oligomers derivatized at the 2'-position with substituents. These oligomers are stable to nuclease activity. Specific 2'-O-substituents which were incorporated into oligonucleotides include ethoxycarbonylmethyl (ester form), and its acid, amide and substituted amide forms.

Martin (*Helvetica Chimica Acta*, 78, 1995, 486–504) discloses certain nucleosides, and oligonucleotides prepared therefrom, that include 2'-methoxyethoxy, 2'-methoxy(tris-ethoxy) and other substituents. Oligonucleotides containing nucleosides substituted with either the 2'-methoxyethoxy and 2'-methoxy(tris-ethoxy)substituents exhibited improved hybridization, as judged by increase in $T_m$.

The use of esters, such as methyl bromoacetate, as electrophiles for the alkylation of nucleosides, have been used where the sugar moiety of the nucleosides being alkylated has been selectively protected. See, PCT application WO 91/06556, entitled "2'-modified oligonucleotides," filed Oct. 24, 1990; and Keller et al., *Helv. Chim. Acta.*, 1993, 76, 884–892.

It has been recognized that oligomeric compounds having improved hybridization and nuclease resistance are of great importance in the development of useful research reagents, diagnostic agents and therapeutic agents. There exists a need in the art for improved processes, for the preparation of 2'-O-modified nucleosidic oligomeric compounds, which are more facile, are faster and are cheaper than processes currently known in the art.

SUMMARY OF THE INVENTION

The present invention provides methods for the regioselective alkylation at the 2'-hydroxy position of a sugar moiety of a nucleoside. These methods are useful for the synthesis of 2'-O-alkyl nucleotides, which in turn serve as precursors in the preparation of oligomeric compounds. The methods of the present invention use nucleosides bearing unprotected 2'- and 3'-hydroxyl functionalities. These nucleosides are treated with a base and alkylated with the reactive form of an ester to form 2'-O-modified nucleosides.

The present invention provides methods for the preparation of a compound of formula:

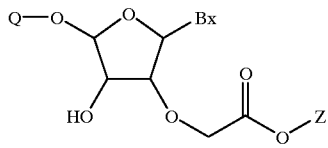

wherein:
Q is H or a hydroxyl protecting group;
Bx is a heterocyclic base moiety; and
Z is $C_1$ to $C_{12}$ alkyl;
comprising the steps of:
(a) selecting a compound of formula:

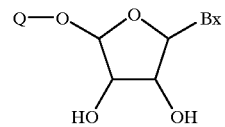

(b) dissolving said compound in at least one solvent to form a solution;
(c) cooling said solution to a temperature of from about 5° C. to about minus 50° C.;
(d) treating said cooled solution with a base to give a mixture;
(e) warming said mixture to a temperature of from about minus 30°° C. to 35°° C.;
(f) cooling said mixture of step (e) to a temperature of from about 5° C. to about minus 50° C.; and
(g) reacting said cooled mixture of step (f) with an ester of the formula:

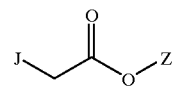

wherein:
Z is as defined above; and
J is a leaving group;
to give said compound.

In a preferred embodiment the heterocyclic base moiety is N3-protected-5-methyluridine, N3-protected-uridine, cytidine, 5-methylcytidine, guanosine, adenosine, or 2,6-diaminopurineriboside.

In another preferred embodiment the base is 1,5-diazabicyclo[4.3.0]non-5-ene, 1,4-diazabicyclo[2.2.2]octane or 1,8-diazabicyclo[5.4.0]undec-7-ene. In yet another preferred embodiment the base is a metal hydride, a metal hydroxide or a metal carbonate. In one preferred embodiment, the metal hydride is sodium hydride, lithium hydride or potassium hydride. In another preferred embodiment, the metal hydroxide is sodium hydroxide, potassium hydroxide or lithium hydroxide. In yet another preferred embodiment, the metal carbonate is sodium carbonate, potassium carbonate or cesium carbonate.

In a further embodiment of the present invention, the solvent is an aprotic solvent. It is preferred that the solvent be dimethylformamide, dimethylsulfoxide, dimethylacetamide, acetonitrile or hexamethylphosphoramide. It is further preferred that a combination of these solvents be used in the methods of the present invention.

Thus it is preferred that the solvent used in the present invention be at least two of dimethylformamide, dimethylsulfoxide, dimethylacetamide, acetonitrile and hexamethylphosphoramide. Most preferably, the solvent is dimethylformamide having from 1% to about 40% dimethylsulfoxide.

It is preferred that the ester be an alkyl haloalkylate. It is further preferred that the ester be an alkyl bromoalkylate. It is most preferred that the ester be methyl bromoacetate.

It is preferred that the cooling of the mixture of the nucleoside and base be to a temperature of from about 5°° C. to about minus 50° C. It is further preferred that the cooling of said mixture be to a temperature of from about minus 30°° C. to about minus 50°° C. It is still further preferred that the cooling of said mixture be to a temperature of from about minus 40°° C. to about minus 50°° C.

The present invention further provides methods for the preparation of a further compound of formula:

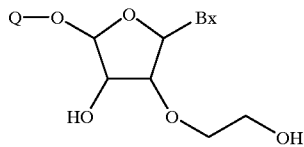

wherein:
Q is H or a hydroxyl protecting group; and
Bx is a heterocyclic base moiety;
comprising treating a compound of formula:

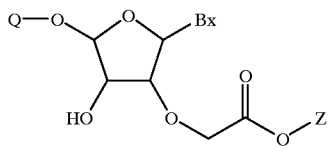

wherein:
Q is H or a hydroxyl protecting group;
Bx is a heterocyclic base moiety; and
Z is $C_1$ to $C_{12}$ alkyl;
with a reducing agent under suitable conditions of time, temperature and pressure.

In a preferred embodiment, the reducing agent is sodium borohydride, lithium borohydride or borane.

The present invention also provides methods for the preparation of a derivative compound of formula:

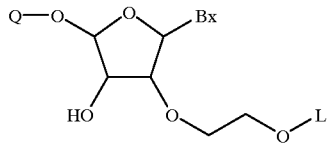

wherein:
Q is H or a hydroxyl protecting group;
Bx is a heterocyclic base moiety;
L is $C_1$ to $C_{10}$ alkyl, —N(R$_1$)R$_2$, or —N=C(R$_1$) (R$_2$);
each R$_1$ and R$_2$ is, independently, H, C$_1$–C$_{10}$ alkyl, a nitrogen protecting group, or R$_1$ and R$_2$, together, are a nitrogen protecting group, or R$_1$, and R$_2$, together, are joined in a ring structure wherein said ring structure comprises at least one heteroatom selected from N and O.

In a preferred embodiment L is —CH$_3$ or —N(CH$_3$)CH$_3$. In another preferred embodiment —N(R$_1$)R$_2$ is phthalimido or piperidinyl. In yet another preferred embodiment R$_1$ and R$_2$ are joined in a ring structure wherein said ring structure comprises at least one heteroatom selected from N and O.

DETAILED DESCRIPTION OF PREFERRED EMBODIMENTS

The present invention provides methods of preferential regioselective alkylation of nucleosides at 2'-hydroxyl positions over 3'-hydroxyl positions. The present methods eliminate protection and subsequent deprotection steps when alkylating the 2'-O-position of nucleosides. The resultant 2'-O-alkylated nucleoside is further reduced to the intermediate 2'-O-hydroxyethyl nucleoside which is further derivatized to 2'-O-modified nucleosides of formula:

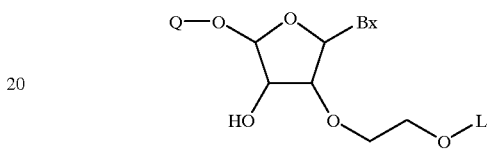

wherein:
Q is H or a hydroxyl protecting group;
Bx is a heterocyclic base moiety; and
L is $C_1$ to $C_{10}$ alkyl, —N(R$_1$)R$_2$, or —N=C(R$_1$) (R$_2$)

The present invention provides improved methods of preparing nucleosides that are useful in the preparation of oligomeric compounds possessing superior hybridization properties. Structure-activity relationship studies have revealed that an increase in binding (T$_m$) of certain 2'-sugar modified oligonucleotides to an RNA target (complement) correlates with an increased "A" type conformation of the heteroduplex. Furthermore, absolute fidelity of the modified oligonucleotides is maintained. Increased binding of 2'-sugar modified sequence-specific oligonucleotides of the invention provides superior potency and specificity compared to phosphorus-modified oligonucleotides such as methyl phosphonates, phosphate triesters and phosphoramidates as known in the literature.

Oligomeric compounds incorporating 2'-O-modified nucleosides of the invention are synthesized by standard solid phase nucleic acid synthesis using automated synthesizers such as Model 380B (Perkin-Elmer/Applied Biosystems) or MilliGen/Biosearch 7500 or 8800. Triester, phosphoramidite, or hydrogen phosphonate coupling chemistries (*Oligonucleotides: Antisense Inhibitors of Gene Expression*. M. Caruthers, p. 7, J. S. Cohen (Ed.), CRC Press, Boca Raton, Fla., 1989) are used with these synthesizers to provide the desired oligonucleotides. The Beaucage reagent (*J. Amer. Chem. Soc.*, 1990, 112, 1253) or elemental sulfur (Beaucage et al., *Tet. Lett.*, 1981, 22, 1859) is used with phosphoramidite or hydrogen phosphonate chemistries to provide 2'-substituted phosphorothioate oligonucleotides.

Unprotected nucleosides are regioselectively alkylated using methods of the present invention. Direct alkylation is faster and less expensive eliminating unnecessary protection, deprotection and purification steps required with other previously reported methods. There has been ample work published on this subject involving activated (Takaku et al., *Chem. Lett.*, 1982, 189–192) and unactivated (Manoharan et al., *Tetrahedron Lett.*, 1991, 32, 7171–7174) electrophiles. The degree of selectivity encompasses a wide range and appears to depend on the substrate and/or the electrophile.

The regioselectivity of the 2'- over the 3'-position of a nucleoside having unprotected 2'- and 3'-hydroxyl groups was initially determined using adenosine and 2,6-diaminopurin-9-yl-riboside. When the unprotected adenosine or 2,6-diaminopurin-9-yl-riboside was reacted with methyl 2-bromoacetate under basic conditions, at low temperatures (approximately −40°° C.), a highly regioselective alkylation of the 2'-versus 3'-hydroxyl position occurred. The regioselectivity for the 2'-over the 3'-position was in a ratio of about 9:1 or better. The resulting products were 2'-O-(methoxycarbonylmethylene)-adenosine and 2'-O-(methoxycarbonylmethylene)-2,6-diaminopurin-9-yl-riboside in about 75% yields. Alkylation of the purine ring was not observed in either of the syntheses, and the regioselectivity in both cases was confirmed by 2D NMR (TOCSY). This highly regioselective alkylation of the unprotected ribosides is thought to be influenced by the effects of the carbonyl group adjacent to the reactive site in this SN2 reaction. Carey, F. A., and Sundberg, R. J., Advanced Organic Chemistry, Part A: Structures and Mechanisms, 1990, 3rd ed., pp. 296–297, Plenum Press, New York, N. Y. The regioselective alkylation reactions were reproduced on multigram scales (25 g), and the small amounts of 3'-O-isomer were readily resolved by chromatography after alkylation or at a subsequent step.

In the context of this invention, the term "oligomeric compound" refers to a plurality of nucleoside monomers joined together in a specific sequence. The nucleosides of use in the present invention may be naturally-occurring or non-naturally occurring. Preferred nucleosides each have a nucleobase attached to a pentose sugar moiety and form oligomeric compounds via phosphorus linkages connecting the sugar moieties. Representative heterocyclic base moities, or nucleobases, include adenine, guanine, adenine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine.

2'-O-Modified nucleosides prepared according to the methods of the present invention are further treated with reagents, using methods well known in the art and illustrated in the examples below, to convert the nucleosides into nucleoside surrogates. Nucleoside surrogates, such as DMT phosphoramidites shown in the examples below, are ready for use in standard oligonucleotide synthesis following well-established protocols. Nucleoside surrogates can include appropriate activated phosphorous atoms in $P^{III}$ or $P^V$ valence states for incorporation into an oligomeric compound. Such activated phosphorous atoms include phosphoramidites, hydrogen phosphonates and triesters. The nucleoside surrogates can also include appropriate hydroxyl blocking groups including, but not limited to, dimethoxytrityl, trimethoxytrityl, monomethoxytrityl and trityl blocking groups, and other blocking groups as are known in the art.

In positioning one of the nucleoside surrogate groups of the invention in an oligonucleotide, an appropriate blocked and activated nucleoside surrogate is incorporated in the oligonucleotides in the standard manner for incorporation of a normal blocked and active standard nucleotide. As for instance, an 2'-O-nucleoside surrogate is selected that has an aminooxy moiety which is protected utilizing a phthalimido protecting group. One of the hydroxyl groups of the surrogate molecule is protected utilizing a dimethoxytrityl protecting group (a DMT protecting group) and the other hydroxyl group is present as a cyanoethoxy diisopropyl phosphoramidite moiety. The surrogate unit is added to the growing oligonucleotide by treating with the normal activating agents, as is known in the art, to react the phosphoramidite moiety with the growing oligomeric compound. This is followed by removal of the DMT group in the standard manner, as is known in the art, and continuation of elongation.

There are a number of modifications that can be made to nucleosides in combination with the 2'-O-modifications of the invention. Representative modifications that can be made to the sugar, base, or to the phosphate group of nucleosides are disclosed in International Publication Numbers WO 91/10671, published Jul. 25, 1991, WO 92/02258, published Feb. 20, 1992, WO 92/03568, published Mar. 5, 1992, and U.S. Pat. Nos. 5,138,045, 5,218,105, 5,223,618 5,359,044, 5,378,825, 5,386,023, 5,457,191, 5,459,255, 5,489,677, 5,506,351, 5,541,307, 5,543,507, 5,571,902, 5,578,718, 5,587,361, and 5,587,469, all assigned to the assignee of this application. The disclosures of each of the above referenced publications are herein incorporated by reference.

The attachment of conjugate groups to oligonucleotides and analogs thereof is well documented in the art. Compounds of the present invention include compounds bearing conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of the present invention, include groups that improve oligomer uptake, distribution, metabolism or excretion. Representative conjugate groups are disclosed in International Patent Application PCT/US92/09196, filed Oct. 23, 1992, U.S. Pat. No. 5,578,718, and U.S. Pat. No. 5,218,105. Each of the foregoing is commonly assigned with this application. The entire disclosure of each is incorporated herein by reference.

Cleavage of oligonucleotides by nucleolytic enzymes requires the formation of an enzyme-substrate complex or, in particular, a nuclease-oligonucleotide complex. The nuclease enzymes will generally require specific binding sites located on the oligonucleotides for appropriate attachment. If the oligonucleotide binding sites are removed or blocked, such that nucleases are unable to attach to the oligonucleotides, the oligonucleotides will be nuclease resistant. In the case of restriction endonucleases that cleave sequence-specific palindromic double-stranded DNA, certain binding sites such as the ring nitrogen in the 3- and 7-positions have been identified as required binding sites. Removal of one or more of these sites or sterically blocking approach of the nuclease to these particular positions within the oligonucleotide has provided various levels of resistance to specific nucleases.

Sugars having O-substitutions on the ribosyl ring are also amenable to the present invention. Representative substitutions for a ring oxygen include S, $CH_2$, CHF, and $CF_2$. See, e.g., Secrist et al., *Abstract 21, Program & Abstracts, Tenth International Roundtable, Nucleosides, Nucleotides and their Biological Applications*, Park City, Utah, Sept. 16–20, 1992, hereby incorporated by reference in its entirety.

Strong bases amenable to the present methods include NaH, 1,5-diazabicyclo[4.3.0]non-5-ene (DBN), 1,4-diazabicyclo[2.2.2]octane (Dabco), 1,8-diazabicyclo[5.4.0]undec-7-ene (DBU), and $CsCO_3$. Other aprotic polar organic solvents may also be used in place of dimethylformamide (DMF), e.g., dimethylsulfoxide, dimethyl-acetamide, acetonitrile, or hexamethylphosphoramide (HMPA).

The present invention provides methods for regioselective alkylation of a nucleoside of the formula:

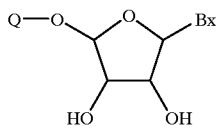

wherein Q and Bx are as described previously.

Selected nucleosides were initially dissolved in one or more solvents. One solvent that worked well was DMF. With insoluble nucleosides, dissolution is first accomplished with gentle heating in DMSO followed by dilution with DMF. In Example 11 below, 2'-O-(methoxycarbonylmethylene)-2,6-diaminopurin-9-yl-riboside was first dissolved in DMSO, with warming, followed by addition of DMF to give 20% DMSO in DMF as the final composition. There are many other solvents and solvent systems that are amenable to the present invention. Some representative solvents include dimethylformamide, dimethylsulfoxide, dimethylacetamide, acetonitrile, or hexamethylphosphoramide and combinations of dimethylformamide, dimethylsulfoxide, dimethylacetamide, acetonitrile, or hexamethylphosphoramide. The solvent used in the methods of the present invention may also be a combination of two or more solvents selected from those stated above.

The solution having the dissolved nucleoside is then cooled to from about 5° C. to about minus 50° C. and treated with a base. Sodium hydride proved effective for a number of reactions that were performed. Other representative bases that are amenable to the methods of the present invention include 1,5-diazabicyclo[4.3.0]non-5-ene, 1,4-diazabicyclo[2.2.2]-octane, 1,8-diazabicyclo[5.4.0]undec-7-ene, or cesium carbonate. The mixture resulting after addition of the base is allowed to warm to from about minus 30°° C. to about 35°° C., and then recooled to from about minus 30°° C. to about minus 50° C. A preferred range is from about minus 40°° C. to about minus 50°° C.

The cooled mixture is next treated with an ester of formula:

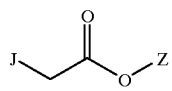

wherein:
Z is $C_1$ to $C_{12}$ alkyl; and
J is a leaving group.

An ester bearing a leaving group at its $\alpha$-$CH_2$ position is the reactive form of the ester. This leaving group is cleaved off the reactive ester when the 2'-hydroxy group of the sugar moiety attacks the $\alpha$-$CH_2$ group of the ester. This results in the formation of a covalent bond between the oxygen atom of the hydroxy group of the sugar moiety and the $\alpha$-$CH_2$ group of the ester.

Leaving groups are routinely used in the art, and include halo, alkoxy, tosylate, brosylate, nosylate, mesylate and triflate. A preferred leaving group is halo. It is more preferred that the leaving group be bromo. A number of esters have been used successfully. It is preferred that the ester used in the methods of the present invention be an alkyl haloalkylate. It is further preferred that the ester be an alkyl bromoalkylate. It is most preferred that the ester be methyl bromoacetate. After the addition of ester, the reaction mixture is allowed to gradually warm to ambient temperature. After stirring at ambient temperature, the reaction mixture is worked up to give the desired 2'-O-esterified nucleoside of formula:

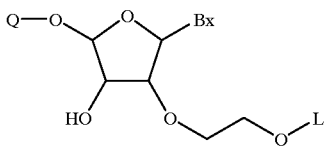

wherein Q, Bx, and L are as previously described.

The 2'-O-esterified nucleoside is further reduced to give the 2'-O-hydroxyethyl compound. A preferred reducing agent is sodium borohydride. A number of other reducing agents are amenable to the present invention, including lithium borohydride and borane. The resultant 2'-O-hydroxyethyl nucleosides are further reacted with reagents to form derivative compounds such as 2'-O-methoxyethyl (2'-O-MOE) and 2'-O-dimethylaminoethyl (DMAOE) nucleosides. The preparation of derivative nucleosides from the 2'-O-hydroxyethyl nucleoside is illustrated in the examples below, and are further disclosed in PCT application PCT/US 98/02405, entitled "Aminooxy-Modified oligonucleotides," filed Feb. 13, 1998.

Nucleosides prepared by the methods of the present invention are useful in the preparation of oligomeric compounds which are utilized as diagnostics, therapeutics and as research reagents and kits. The oligomeric compounds can be utilized in pharmaceutical compositions by adding an effective amount to a suitable pharmaceutically acceptable diluent or carrier. The oligomeric compounds prepared according to the methods of the present invention can be used for treating organisms having a disease characterized by the undesired production of a protein. The organism can be contacted with an oligomeric compound which incorporates nucleosides prepared by the present methods. The oligomeric compound is synthesized to have a sequence that is capable of specifically hybridizing with a strand of target nucleic acid that codes for the undesirable protein.

EXAMPLES

General

All reagents and solvents were purchased from Aldrich Chemicals unless otherwise stated. Reactions were performed under an argon atmosphere unless otherwise noted. Column chromatography was carried out using normal phase silica gel. Eluent solvent ratios are given as volume/volume. Solvent gradients were carried out stepwise. Evaporations of solvents were performed in vacuo (50 torr) at 35°° C. unless otherwise specified. Adenosine deaminase (2–5 units/mg) was purchased from Reliable Biopharmaceuticals. NMR spectra were obtained with the following instruments: $^1$H NMR: Varian Gemini-200 (199.975 MHZ) or Varian Unity 400 (399.952 MHZ). $^{13}$C NMR: Varian Gemini-200 (50.289 MHZ). $^{31}$P NMR: Varian Gemini-200 (79.990 MHZ). NMR spectra were recorded using either deuteriochloroform, dimethylsulfoxide-d$_6$, dimethylformamide-d$_7$, or deuteriomethanol as solvent (tetramethylsilane as internal standard). The following abbreviations were used to designate the multiplicity of individual signals: s=singlet, d=doublet, t=triplet, q=quartet, m=multiplet, dd=doublet of doublets, br s=broad singlet. Mass spectra were performed by Mass Consortium, San Diego, Calif.

Example 1

2'-O-(Methoxycarbonylmethylene)adenosine

Adenosine (25.0 g, 93.5 mmol) was dissolved in DMF (900 mL) under an argon atmosphere. The resulting solution was cooled to −50°° C., NaH (60% dispersion in mineral oil) (4.86 g, 122 mmol) was added in two portions, and the reaction mixture was allowed to warm to −30° and stirred for 30 minutes. After recooling the reaction mixture to −50°° C., methyl 2-bromoacetate (11.5 mL, 122 mmol) was added dropwise, and the reaction was allowed to warm to ambient temperature. After stirring at ambient temperature for 1 hour, MeOH (100 mL) was added, the reaction was stirred for 10 minutes, and the solvent was evaporated in vacuo to give a foam. The product was coevaporated with EtOAc to afford the title compound as a crude solid which was of sufficient purity for use without further purification in subsequent reactions. A small portion of the product was purified by column chromatography and characterized. $^1$H NMR (DMSO-d$_6$): δ 3.48 (s, 3H), 3.56–3.59 (m, 2H), 4.0 (m, 1H), 4.21 (q $_{a,b}$, 2H, J$_{a,b}$=17 Hz), 4.38 (dd, 1H), 5.63 (dd, 1H), 5.29 (d, 1H), 5.40 (dd, 2H), 6.02 (d, 1H), 7.37 (bd, 2H), 8.12 (s, 1H), 8.28 (s, 1H). HRMS (FAB) calcd for C$_{13}$H$_{17}$N$_5$O$_6$+ H$^+$: 340.1257; found: 340.1257. 2D-$^1$H NMR (TOCSY) confirmed 2'-O-alkylation.

Example 2

5'-O-t-Butyldiphenylsilyl-2'-O-(methoxycarbonylmethylene)-adenosine

2'-O-(Methoxycarbonylmethylene)adenosine (23 g, 67.8 mmol) as a crude material was dissolved in dry pyridine (500 mL), t-butyldiphenylsilyl chloride (21.2 mL, 81.3 mmol) was added, and the reaction mixture was stirred for 15 hours at ambient temperature. The solvent was evaporated in vacuo to a volume of 250 mL, EtOAc (1 L) was added and the solution was washed with water (200 mL), then brine (100 mL), and dried with MgSO$_4$. The solvent was evaporated in vacuo to give a residue which was dissolved in a minimum amount of EtOAc (40 mL), and this solution was added dropwise to a vigorously stirred solution of hexanes (4 L) to give a precipitate. The mixture was allowed to settle for 12 hours after which time the supernatent was decanted off, and the solid was filtered and washed with hexanes twice to give the title compound as a solid (46.68 g). A small portion of the product was purified by column chromatography and characterized.

$^1$H NMR (DMSO-d$_6$): δ 1.01 (s, 9H), 3.55 (s, 3H), 3.72–3.98 (m, 2H), 4.05 (m, 1H), 4.19–4.39 (dd, 2H), 4.53 (dd, 1H), 4.70 (t, 1H), 5.40 (d, 1H), 6.09 (d, 1H), 7.24–7.63 (m, 12H), 8.04 (s, 1H), 8.23 (s, 1H).

Example 3

5'-O-t-Butyldiphenylsilyl-2'-O-(hydroxyethyl) adenosine

5'-O-t-Butyldiphenylsilyl-2'-O-(methoxycarbonyl methylene)adenosine (46.68 g, 80.80 mmol) was dissolved in CH$_2$Cl$_2$, (200 mL), EtOH (200 proof, 500 mL) was added, the reaction was cooled to 5°° C., and NaBH$_4$ (6.12 g, 162 mmol) was carefully added in 3 portions. After stirring for 2 hours at 5° C., the reaction was allowed to warm to ambient temperature and stirred for 16 hours after which the solvent was evaporated to a volume of 170 mL. EtOAc (850 mL) was added, the solution was washed with water (200 mL), then with brine (100 mL), and the organic solution was dried with MgSO$_4$. The solvent was evaporated in vacuo to give a residue. The residue was purified by column chromatography using CH$_2$Cl$_2$—EtOAc—MeOH, 78:20:2, then CH$_2$Cl$_2$—EtOAc—MeOH, 75:20:5, to give the title compound as a solid (22.71 g, 44% over 3 steps).

$^1$H NMR (DMSO-d$_6$): δ 1.02 (s, 9H), 3.42–3.62 (m, 4H), 3.72–4.09 (m, 3H), 4.43 (dd, 1H), 4.60 (t, 1H), 4.78 (t, 1H), 5.21 (d, 1H), 6.03 (d, 2H), 7.25–7.64 (m, 11H), 8.09 (s, 1H), 8.24 (s, 1H). 2D-$^1$H NMR (TOCSY) confirmed 2'-O-alkylation.

Example 4

5'-O-t-Butyldiphenylsilyl-N6-benzoyl-2'-O-(hydroxyethyl)-adenosine

Dried 5'-O-t-butyldiphenylsilyl-2'-O-(hydroxyethyl)-adenosine (24 g, 43.7 mmol) was dissolved in anhydrous pyridine (500 mL) under inert atmosphere, and trimethyl-chlorosilane (27.7 mL, 218 mmol) was added at 0° C. The reaction was allowed to warm to ambient temperature, stirred for 1 hour, then cooled to 0° C. Benzoyl chloride (25.3 mL, 218 mmol) was added dropwise, then the reaction was allowed to warm to ambient temperature and stirred for 4 hours after which it was cooled to 0° C. and water (100 mL) was added. After stirring for 10 minutes aqueous 30% NH$_4$OH (100 mL) was added, and the reaction was stirred at 0° C. for 1 hour. The solvent was evaporated in vacuo to give a residue which was dissolved in EtOAc (1 L), and the resulting solution was washed with water (200 mL) twice, then with brine (100 mL). The organic solution was dried with MgSO$_4$, and the solvent was evaporated in vacuo to give a residue. The residue was purified by column chromatography using CH$_2$Cl$_2$—EtOAc—MeOH, 70:27:3, to give the title compound as a solid (23.77 g, 83%).

$^1$H NMR (DMSO-d$_6$): δ 11.23 (br s, 1H), 8.68 (s, 1H), 8.62 (s, 1H), 7.3–8.1 (m, 15H), 6.20 (d, 1H, J$_{1',2'}$=4.9 Hz), 5.30 (d, 1H), 4.73 (m, 2H), 4.55 (m, 1H), 4.09 (m, 1H), 3.87 (m, 2H), 3.55 (m, 4H), 0.98 (s, 9H). LRMS (FAB) m/z: 654 (M+H)$^+$, 676 (M+Na)$^+$.

Example 5

5'-O-t-Butyldiphenylsilyl-N6-benzoyl-2'-O-(phthalimido-N-oxyethyl)adenosine

5'-O-t-Butyldiphenylsilyl-N6-benzoyl-2'-O-(hydroxy-ethyl)adenosine (5.77 g, 8.83 mmol) was mixed with triphenylphosphine (3.01 g, 11.48 mmol) and N-hydroxyphthalimide (1.87 g, 11.48 mmol), and the mixture was dried over P$_2$O$_5$ in vacuo at 40° C. for two days.

The dried material was dissolved in anhydrous THF (88 mL) under argon atmosphere. Diethylazodicarboxylate (1.81 mL, 11.48 mmol) was added dropwise such that the resulting deep red color just discharged before further addition. After the addition was completed, the reaction was stirred for 4 hours and the solvent was evaporated in vacuo and the residue dissolved in EtOAc (450 mL). The organic solution was washed with water (90 mL), brine (90 mL), dried over $MgSO_4$, and the solvent was evaporated in vacuo to give a residue which was purified by column chromatography using $CH_2Cl_2$-EtOAc, 60:40, to give the title compound as a solid (4.37 g, 62%).

$^1$H NMR (DMSO-$d_6$): δ 8.60 (s, 1H), 8.58 (s, 1H), 7.3–8.1 (m, 19H), 6.14 (d, 1H, $J_{1',2'}$=5.0 Hz), 5.32 (d, 1H), 4.76 (m, 1H), 4.55 (m, 1H), 4.31 (m, 2H), 3.7–4.0 (m, 5H), 0.96 (s, 9H). $^{13}$C NMR (CDCl$_3$): δ 164.7, 163.8, 152.9, 151.9, 149.9, 142.2, 135.9, 134.9, 134.3, 133.5, 133.3, 132.9, 132.5, 132.3, 132.1, 130.1, 129.1, 128.8, 124.0, 87.7, 85.5, 83.1, 77.9, 69.9, 69.5, 63.8, 27.3, 19.6. LRMS (FAB) m/z: 799 (M+H)$^+$, 821 (M+Na)$^+$.

Example 6

5'-O-t-Butyldiphenylsilyl-N6-benzoyl-2-O-(methyleneimino-oxyethyl)adenosine

5'-O-t-Butyldiphenylsilyl-N6-benzoyl-2'-O-(phthalimido-N-oxyethyl)adenosine (17.97 g, 22.49 mmol) was dissolved in $CH_2Cl_2$ (100 mL) and MeOH (75 mL), the mixture was cooled to 5° C. and N-methylhydrazine (1.32 mL, 24.74 mmol) was added. After stirring the reaction for 1 hour at 5° C. there was a white precipitate which was filtered and washed with cold $CH_2Cl_2$. The filtrate was evaporated in vacuo at less than 25° C. to give the 2'-O-aminooxyethyl derivative as a crude residue which was dissolved in MeOH (225 mL). Formaldehyde (37% aqueous solution, 1.68 mL, 22.5 mmol,) was added, and the reaction mixture was stirred at ambient temperature for 1 hour. The solvent was evaporated in vacuo to give an oil which was purified by column chromatography using $CH_2Cl_2$-EtOAc, 75:25, then $CH_2Cl_2$—EtOAc—MeOH, 74:24:2, to give the title compound as a white foam (9.82 g, 64%).

$^1$H NMR (CDCl$_3$): δ 9.15 (br s, 1H), 8.78 (s, 1H), 8.31 (s, 1H), 7.3–8.1 (m, 15H), 7.02 (d, 1H, J=7.9 Hz), 6.46 (d, 1H, J=7.9 Hz), 6.24 (d, 1H, $J_{1',2'}$=4.0 Hz), 4.59 (m, 2H), 4.26 (m, 3H), 4.07 (m, 2H), 3.87 (m, 2H), 1.11 (s, 9H). $^{13}$C NMR (CDCl$_3$): δ 164.6, 152.7, 151.5, 149.6, 141.6, 138.0, 135.6, 135.5, 132.6, 132.0, 131.9, 129.9, 128.7, 128.3, 127.8, 123.6, 87.1, 85.2, 82.5, 72.7, 70.1, 69.3, 63.4, 27.0, 19.2. LRMS (FAB+) m/z: 681 (M+H)$^+$.

Example 7

5'-O-t-Butyldiphenylsilyl-N6-benzoyl-2'-O-(dimethylaminooxy-ethyl)adenosine

5'-O-t-Butyldiphenylsilyl-N6-benzoyl-2'-O-(methyleneiminooxyethyl)adenosine (9.82 g, 14.42 mmol) was dissolved in a solution of 1M pyridinium p-toluenesulfonate (PPTS) in MeOH (144 mL) with protection from moisture. NaCNBH$_3$ (1.81 g, 28.8 mmol) was added at 5° C., the reaction mixture was allowed to warm to ambient temperature and stirred for 2 hours. 5% aqueous NaHCO$_3$ was added to pH 7, the mixture was extracted with EtOAc (3×200 mL), and the organic solution was dried over MgSO$_4$. The solvent was evaporated in vacuo to give a residue which was dissolved in a solution of 1M PPTS in MeOH (144 mL). Formaldehyde (37% aqueous solution, 1.19 mL, 15.9 mmol) was added to the reaction mixture, and it was stirred at ambient temperature for 30 minute. NaCNBH$_3$ (1.81 g, 28.8 mmol) was then added at 5° C., and the reaction mixture was allowed to warm to ambient temperature. After stirring for 2 hours, the pH was adjusted to 7 by addition of 5% aqueous NaHCO$_3$, the mixture was extracted with ethyl acetate (3×200 mL), and the organic solution was dried with MgSO$_4$. The solvent was evaporated in vacuo to give a solid which was purified by column chromatography using $CH_2Cl_2$-EtOAc, 75:25, then $CH_2Cl_2$—EtOAc—MeOH, 74:24:2, to give the title compound as a white foam (7.80 g, 78%).

$^1$H NMR (CDCl$_3$): δ 9.09 (br s, 1H), 8.78 (s, 1H), 8.31 (s, 1H), 7.4–8.1 (m, 15H), 6.23 (d, 1H, $J_{1',2'}$=3.7 Hz), 4.55 (m, 2H), 4.30 (m, 1H), 4.21 (m, 1H), 4.07 (m, 2H), 3.93 (m, 1H), 3.86 (m, 2H), 3.72 (m, 1H), 2.62 (s, 6H), 1.11 (s, 9H). $^{13}$C NMR (CDCl$_3$): δ 152.7, 149.5, 141.7, 135.6, 132.6, 132.0, 131.8, 129.8, 128.8, 128.5, 128.3, 87.2, 85.3, 82.6, 70.9, 70.1, 69.5, 63.5, 47.5, 27.0, 19.2. LRMS (FAB+) m/z: 697 (M+H)$^+$, 719 (M+Na)$^+$.

Example 8

N6-Benzoyl-2'-O-(dimethylaminooxyethyl) adenosine

5'-O-t-Butyldiphenylsilyl-N6-benzoyl-2'-O-(dimethylaminooxyethyl)adenosine (7.77 g, 11.15 mmol) was dissolved in THF (110 mL), and tetrabutylammonium fluoride (TBAF)on silica (1.0–1.5 mmol/g silica, 10.1 g) was added. After stirring for 24 hours the solid was filtered, washed with THF, and the solvent was evaporated in vacuo to give a solid which was purified by column chromatography using $CH_2Cl_2$—EtOAc—MeOH, 75:20:5, to give the title compound as a solid (4.42 g, 86%).

$^1$H NMR (DMSO-$d_6$): δ 8.76 (s, 1H), 8.75 (s, 1H), 7.5–7.7 (m, 5H), 6.16 (d, 1H, $J_{1',2'}$=6.0 Hz), 5.27 (d, 1H), 5.17 (m, 1H), 4.62 (m, 1H), 4.35 (m, 1H), 4.02 (m, 1H), 3.66 (m, 6H), 2.34 (s, 6H). $^{13}$C NMR (CDCl$_3$): δ 164.7, 151.9, 150.5, 150.3, 143.3, 133.3, 132.8, 128.7, 127.9, 124.5, 89.5, 88.0, 82.2, 70.7, 70.0, 63.1, 47.4. LRMS (FAB+) m/z: 459 (M+H)$^+$, 481 (M+Na)$^+$.

Example 9

5'-O-(4,4'-Dimethoxytrityl)-N6-benzoyl-2'-O-(dimethyl-aminooxyethyl)adenosine

N6-Benzoyl-2'-O-(dimethylaminooxyethyl)adenosine (4.4 g, 9.60 mmol) was coevaporated with anhydrous pyridine twice, DMAP (117 mg, 0.96 mmol) was added, and the mixture was dissolved in anhydrous pyridine (100 mL). 4,4'-Dimethoxytrityl chloride (DMTCl, 3.58 g, 10.56 mmol) was added, and after stirring for 16 hours the solvent was evaporated in vacuo to give an oil which was dissolved in EtOAc (400 mL). The organic solution was washed with water (80 mL) and brine (40 mL), NEt$_3$ (4 mL) was added to the organic phase, and it was dried with MgSO$_4$. The solvent was evaporated in vacuo to give a foam which was purified by column chromatography (silica pretreated with 1% NEt$_3$) using and $CH_2Cl_2$—EtOAc—MeOH—NEt$_3$, 78:20:2:1, to afford the title compound as a foam (6.9 g, 95%).

$^1$H NMR (CDCl$_3$): δ 9.07(br s, 1H), 8.75 (s, 1H), 8.24 (s, 1H), 6.8–8.1 (m, 18H), 6.21 (d, 1H), $J_{1',2'}$=4.5 Hz), 4.70 (m, 1H), 4.49 (m, 1H), 4.28 (m, 2H), 4.06 (m, 1H), 3.86 (m, 3H), 3.79 (s, 6H), 3.47 (m, 2H), 2.61 (s, 6H). $^{13}$C NMR (CDCl$_3$): δ 164.7, 158.4, 152.5, 151.4, 149.5, 144.4, 141.8, 135.5, 133.5, 132.5, 129.9, 128.6, 128.0, 127.8, 126.8, 123.4, 87.1, 86.4, 84.2, 82.2, 70.8, 69.9, 63.1, 55.0, 47.4. LRMS (FAB+) m/z: 893 (M+Cs)+.

Example 10

5'-O-(4,4'-Dimethoxytrityl)-N6-benzoyl-2'-O-(dimethylaminooxyethyl)adenosine-3'-(2-cyanoethyl-N,N-diisopropylphosphoramidite)

5'-O-(4,4'-Dimethoxytrityl)-N6-benzoyl-2'-O-(dimethylaminooxyethyl)adenosine (5.0 g, 6.57 mmol) was dissolved in anhydrous $CH_2Cl_2$ (70 mL) and diisopropylamine tetrazolide (1.24 g, 7.23 mmol) and 2-cyanoethyl-N,N,N',N'-tetraisopropylphosphorodiamidite (2.51 mL, 7.89 mmol) were added. After several hours EtOAc (600 mL) and $NEt_3$ (6 mL) were added and the organic solution was washed with saturated $NaHCO_3$ twice (120 mL, 70 mL), then with brine twice (2×70 mL), and the organic phase was dried with $MgSO_4$. The solvent was evaporated in vacuo at 27° C. to give an oil which was purified by column chromatography (silica pretreated with 1% $NEt_3$) using EtOAc—$NEt_3$, 99:1, to afford the title compound as a foam (4.34 g, 69%).

$^{31}$P NMR ($CDCl_3$): δ 151.2, 150.6. LRMS (FAB+) m/z: 1093 (M+Cs)+. HRMS (FAB): calcd for $C_{51}H_{61}N_8O_9P$: 960.4377; found: 960.4377

Example 11

2'-O-(Methoxycarbonylmethylene)-2,6-diaminopurin-9-yl-riboside 2,6-Diaminopurin-9-yl-riboside (25.00 g, 88.6 mmol) was dissolved in anhydrous DMSO (90 mL) with gentle heating to give a brown solution which was then diluted with anhydrous DMF (355 mL). The reaction mixture was cooled to 5° C., NaH (60% oil dispersion) (6.20 g, 155 mmol) was added, and the reaction mixture was allowed to warm to ambient temperature and stirred for 1 hour. The resultant suspension was cooled to −40° C. in an $CH_3CN$—$CO_2(s)$ bath and methyl 2-bromoacetate (14.29 mL, 155 mmol) was added slowly. The reaction mixture was allowed to slowly warm to ambient temperature over 1 hour. After 17 hours glacial AcOH (6 mL) was added dropwise to give a solution with pH 4. The solvent was evaporated in vacuo (1 torr) at 45° C. to give an amorphous mass to which $CH_2Cl_2$ (400 mL) was added. The mixture was mechanically stirred for 15 minutes to give a suspension to which hexanes (400 mL) was slowly added. Upon standing for 15 minutes the solid settled from the suspension. The supernatant was decanted and the solid was washed with hexanes thrice (3×200 mL) then dissolved in $H_2O$ (250 mL). The aqueous was extracted with ether thrice (3×100 mL) which resulted in an emulsion within the organic. The organic was then washed with $H_2O$ twice (2×100 mL) and the aqueous portions were combined. The $H_2O$ was removed by evaporation at 45° C. to give a residue (62 g) which was utilized as starting material for the next step. A small portion of product was dissolved in MeOH, adsorbed unto silica and was purified by column chromatography using and $CH_2Cl_2$—MeOH, 85:15, to give the title compound as a white solid. $^1$H NMR (DMSO-$d_6$): δ 7.91 (s, 1H), 6.76 (br s, 2H), 5.87 (d, 1, $J_{1',2'}$=6.8 Hz), 5.73 (br s, 2H), 5.39 (m, 1H), 5.21 (d, 1H), 4.52 (m, 1H), 4.29 (m, 1H), 4.20 ($q_{a,b}$, 2H, $J_{a,b}$=16.8 Hz), 3.92 (m, 1H), 3.55 (m, 2H), 3.53 (s, 3H). $^{13}$C NMR ($CD_3OD$) 172.6, 161.3, 157.7, 152.0, 139.1, 115.0, 88.7, 88.0, 83.4, 71.1, 68.6, 63.4, 52.4. HRMS (FAB) calcd for $C_{13}H_{18}N_6O_6$+H+: 355.1362; found: 355.1366. 2D-$^1$H NMR (TOCSY) confirmed 2'-O-alkylation.

Example 12

2'-O-(Methoxycarbonylmethylene)guanosine

2'-O-(Methoxycarbonylmethylene)-2,6-diaminopurin-9-yl-riboside (112 g, 159 mmol) as a crude material was suspended in 0.1 M $NaPO_4H_2$ (810 mL, pH 7.0), and the pH was adjusted using a digital meter to 7.4 with concentrated HCl (optionally 2N NaOH) to give a suspension. Adenosine deaminase (810 mg, 1620 U) was added, and the reaction mixture was mechanically stirred gently at 39° C. to give a fine suspension. After 1.5 hours the pH was 6.7 and was adjusted to pH 7.0 with 2 N NaOH. After 4 hours the pH was adjusted again to 7.0 with 2 N NaOH. After 21 hours the pH was 7.7 and the pH was adjusted several times to 7.0 with 2N HCl. After 34 hours the reaction mixture was a brown solution with pH 9.2. The pH was adjusted to 7.0 with conc HCl several more times. After 60 hours TLC ($CH_2Cl_2$—MeOH, 85:15) indicated the absence of starting material and presence of a major spot (putative 2'-O-carboxylate derivative of guanosine) at origin. The solvent was evaporated in vacuo at 42° C. to give a viscous mass which was shaken and coevaporated with $CH_3CN$ (400 mL) to give a slurry/gum. This treatment was repeated two additional times to remove water affording the product as small pellets (148 g). The crude product was suspended in MeOH (1.6 L), and the pH was adjusted to 0.5 with conc sulfuric acid while mechanically stirred to give a fine suspension. The pH was adjusted to 0.5 two additional times over several hours. After 20 hours in acidic media the pH was 1.0 and the pH was adjusted to 0.5. After about 20 hours in acidic media the pH was 0.5. The reaction mixture was cooled to 5° C. and pyridine (330 mL) was slowly added to give a mixture with pH 4.5. The solvent was evaporated in vacuo to give a viscous liquid which was shaken and coevaporated with anhydrous pyridine (500 mL) to remove water. This treatment was repeated two additional times, and the product was dried in vacuo (0.1 torr) at 40° C. for 24 hours to give a solid (169 g, 177 mmol) which was utilized in the next step without further purification. A small portion of the product was dissolved in MeOH, adsorbed unto silica and purified by column chromatography using $CH_2Cl_2$—MeOH, 85:15, to give the title compound as a white solid.

$^1$H NMR (DMSO-$d_6$): δ 7.91 (s, 1H), 6.51 (br s, 2H), 5.83 (d, 1H, $J_{1',2'}$=6.4 Hz), 5.24 (d, 1H), 5.05 (m, 1H), 4.44 (m, 1H), 4.27 (m, 1H), 4.22 ($q_{ab}$, 2, $J_{a,b}$=16.8 Hz), 3.89 (m, 1H), 3.56 (s, 3H), 3.50 (m, 2H). $^{13}$C NMR (DMSO-$d_6$): δ 170.4, 156.7, 153.8, 151.4, 135.5, 116.5, 85.8, 84.1, 81.3, 68.8, 66.7, 61.3, 51.5. HRMS (FAB) calcd for $C_{13}H_{17}N_5O_7$+Na+: 378.1026; found: 378.1026. Anal. Calcd for $C_{13}H_{17}N_5O_7$ $HSO_4Na$: C, 32.85; H, 3.82; N, 14.73; found: C, 33.28, H, 3.83, N, 14.44. 2D-$^1$H NMR (TOCSY) confirmed 2'-O-alkylation.

Example 13

5'-O-t-Butyldiphenylsilyl-2-O-(methoxycarbonylmethylene)-guanosine

2'-O-(Methoxycarbonylmethylene)guanosine (159 g, 166 mmol) as a dried crude product was suspended in anhydrous pyridine (1000 mL). The mixture was stirred for several hours to give a fine suspension, then cooled to 5° C. and t-butylchlorodiphenylsilane (125 mL, 481 mmol) was added slowly. The reaction mixture was allowed to warm to ambient temperature, and after 4 hours additional t-butylchlorodiphenylsilane (38.7 mL, 149 mmol) was added. After an additional 24 hours MeOH (125 mL, 830 mmol) was added to the reaction mixture, and after stirring for 15 minutes the solvent was evaporated in vacuo to give a mass which was suspended in EtOAc (1500 mL) and water (400 mL). The mixture was shaken and allowed to partition over 20 minutes, the organic was separated, washed with water (200 mL) and then with brine (200 mL). The aqueous washes were combined, extracted with EtOAc thrice (3×330 mL), and the organic extracts were washed with brine (200 mL). The organic extracts were dried with $Na_2SO_4$ and the solvent was evaporated in vacuo to give an oil which was dissolved in EtOAc (150 mL). This solution was slowly poured into stirred hexanes (3 L) to give a suspension which was stirred for 1 hour. The solid was filtered, washed with hexanes thrice, and dried in vacuo at ambient temperature to give a solid (94 g). The crude product was dissolved in $CH_2Cl_2$ (150 mL) and purified by column chromatography using $CH_2Cl_2$, then $CH_2Cl_2$—MeOH, 90:10, to afford the title compound as a foam (41.3 g, 42% overall yield).

$^1$H NMR (CDCl$_3$): δ 7.2–7.8 (m, 11H). 6.50 (br s, 2H), 6.01 (d, 1H, $J_{1',2'}$=4.0 Hz), 3.55–4.48 (m, 8H), 3.67 (s, 3H), 1.04 (s, 9H). $^{13}$C NMR (CDCl$_3$): δ 171.4, 158.8, 153.8, 151.3, 135.5, 135.3, 132.8, 132.5, 129.8, 127.7, 127.2, 117.0, 85.9, 84.5, 84.2, 69.1, 68.3, 63.4, 52.2, 26.8, 19.1. HRMS (FAB) calcd for $C_{29}H_{35}N_5O_7Si+H^+$: 594.2384; found: 594.2390.

Example 14

5'-O-t-Butyldiphenylsilyl-2'-O-(hydroxyethyl) guanosine

5'-O-t-Butyldiphenylsilyl-2-O-(methoxycarbonylmethylene)guanosine (41.26 g, 69.5 mmol) was dissolved in anhydrous EtOH, the solution was cooled to 5° C., and NaBH$_4$ (5.26 g, 139 mmol) was added slowly over several minutes. The reaction mixture was allowed to slowly warm to ambient temperature over 30 minutes, and after 2 hours the pH was adjusted to 5 by slow addition of glacial ACOH (25 mL). The solvent was evaporated in vacuo to give an oil which was dissolved in EtOAc (2000 mL). The organic was washed with water thrice (3×200 mL) (addition of brine was at times necessary for phase separation), washed with brine (200 mL), dried with MgSO$_4$, and the solvent was evaporated in vacuo to give a foam. To remove water the product was coevaporated in vacuo with anhydrous pyridine (2×500 mL) twice, then dried in vacuo (0.1 torr) at ambient temperature for 12 hours to give the title compound as a crude foam (59.6 g) which was used for the following reaction. A small amount of product was purified by column chromatography using $CH_2Cl_2$—MeOH, 87:13, and characterized.

$^1$H NMR (DMSO-d$_6$): δ 7.4–7.6 (m, 10H), 6.50 (br s, 2H), 5.82 (d, 1, $J_{1',2'}$=4.4 Hz), 5.80 (br s, 1H), 5.18 (m, 1H), 4.76 (m, 1H), 4.35 (m, 2H), 3.97 (m,1H), 3.82 (m, 2H), 3.56 (m, 3H), 0.98 (s, 9H). HRMS (FAB) calcd for $C_{28}H_{35}N_5O_6Si+H^+$: 566.2435; found: 566.2449.

Example 15

5'-O-t-Butyldiphenylsilyl-N2-isobutyryl-2'-O-(hydroxyethyl)-guanosine

Dried 5'-O-t-butyldiphenylsilyl-2'-O-(hydroxyethyl)-guanosine (55.9 g, <69 mmol) as a crude product was dissolved in anhydrous pyridine (494 mL, 6.11 mol) with cooling to 5° C. and trimethylchlorosilane (62.7 mL, 494 mmol) was added slowly to give a suspension. The reaction mixture was allowed to slowly warm to ambient temperature, and after 1 hour was again cooled to 5° C. Isobutyryl chloride (51.8 mL, 494 mmol) was added and the reaction mixture was allowed to warm to ambient temperature. After 2 hours the reaction mixture was cooled to 5° C. and cold water (100 mL) was slowly added. After stirring for 12 hours, the solvent was evaporated in vacuo at 40° C. to give an oil which was dissolved in EtOAc (2000 mL) and water (200 mL). The mixture was shaken, the organic was separated, washed twice with water (2×200 mL), then with brine (200 mL), and dried with MgSO$_4$. The solvent was evaporated in vacuo to a volume of about 500 mL after which there was a flocculent white solid which was filtered, washed with cold EtOAc (3×5 mL), and dried in vacuo (0.5 torr) at 45° C. with $P_2O_5$ for 28 hours to afford the title compound as a white solid (26.74 g, 60%).

$^1$H NMR (DMSO-d$_6$): δ 8.15 (s, 1H), 7.3–7.6 (m, 10H), 5.96 (d, 1H, $J_{1',2'}$=4.4 Hz), 5.25 (d, 1H), 4.80 (m, 1H), 4.45 (m, 2H), 4.05 (m, 1H), 3.87 (m, 2H), 3.56 (m, 4H) 2.77 (m, 1H), 1.13 (d, 6H), 1.00 (s, 9H). $^{13}$C NMR (DMF-d$_7$): δ 181.1, 155.7, 149.6, 149.3, 138.0, 136.1, 136.0, 133.8, 133.6, 130.6, 128.5, 121.5, 86.4, 85.9, 82.6, 73.0, 70.1, 64.8, 61.5, 27.0, 19.5, 19.1. HRMS (FAB) calcd for $C_{32}H_{41}N_5O_7Si+H^+$: 636.2854; found: 636.2839. Anal. Calcd for $C_{32}H_{41}N_5O_7Si$: C, 60.45; H, 6.50; N, 11.02; found: C, 60.47, H, 6.51, N, 10.88.

Example 16

5'-O-t-Butyldiphenylsilyl-N2-isobutyryl-2'-O-(phthalimido-N-oxyethyl)guanosine

Dried 5'-O-t-butyldiphenylsilyl-N2-isobutyryl-2-O-(hydroxyethyl)guanosine (12.72 g, 20.0 mmol) was dissolved in anhydrous THF (200 mL) followed by addition of PPh$_3$ (6.296 g, 24.0 mmol) and N-hydroxyphthalimide (3.916 g, 24.0 mmol). The reaction mixture was cooled to 5° C. and diethylazodicarboxylate (3.78 mL, 24 mmol) was added slowly. The reaction mixture was allowed to warm to ambient temperature and after 2.5 hours the solvent was evaporated in vacuo at 25° C. to give a gel. The product was dissolved in $CH_2Cl_2$ and purified by column chromatography using $CH_2Cl_2$—MeOH, 94:6, then $CH_2Cl_2$—MeOH, 92:8, to give the title compound as a foam (21.0 g, 17.0 mmol, 85%, corrected yield) which was contaminated with POPh$_3$ (1 mol-eq) and EtOCONNCO$_2$Et (1 mol-eq) based on $^1$H NMR. The product also contained a side product (25%) resulting from ring-opening of the phthalimido group by MeOH (characterized by LRMS(ES)) which deprotects to afford the correct product in the following reaction. A small amount of product was purified by column chromatography and characterized.

$^1$H NMR (DMSO-d$_6$): δ 8.12 (s, 1H), 7.3–7.8 (m, 14H), 5.89 (d, 1H, $J_{1',2'}$=3.0 Hz), 5.24 (d, 1H), 4.51 (m, 1H), 4.42 (m, 1H), 4.29 (m, 2H), 3.7–4.0 (m, 5H), 3.95 (m, 2H), 3.82 (m, 2H) 3.74 (m, 1H), 2.71 (m, 1H), 1.10 (d, 6H), 0.97 (s, 9H). $^{13}$C NMR (CDCl$_3$): δ 179.3, 163.8, 156.8, 155.5, 148.1, 136.6, 135.5, 135.4, 134.8, 132.1, 131.9, 129.9, 128.5, 128.3, 127.8, 127.6, 127.6, 123.7, 121.5, 85.8, 84.8, 83.8, 69.2, 68.9, 63.4, 36.0, 26.8, 18.8, 14.3. HRMS (FAB) calcd for $C_{40}H_{44}N_6O_9Si+Cs^+$: 913.1993; found 913.1965. 2D-$^1$H NMR (TOCSY) confirmed 2'-O-alkylation.

Example 17

5'-O-t-Butyldiphenylsilyl-N2-isobutyryl-2-O-(methyleneimino-N-oxyethyl)guanosine 5'-O-t-Butyldiphenylsilyl-2'-O-(phthalimido-N-oxyethyl)guanosine (58.74 g, 47.6 mmol, corrected) containing impurities was dissolved in $CH_2Cl_2$ (470 mL), the solution was cooled to 5° C. and N-methylhydrazine (2.78 mL, 52.4 mmol) was added. After stirring at 5° C. for 1 hour, there was a white suspension, and additional N-methylhydrazine (2.78 mL, 52.4 mmol) was added at 5° C. After an additional hour at 5° C., the white solid was filtered, and washed with $CH_2Cl_2$ thrice. Toluene (250 mL) was added and the solvent was evaporated in vacuo at 26° C. to give the aminooxy derivative 19 as a foam. The crude product was dissolved in anhydrous MeOH (470 mL), 37% $CH_2O$—$H_2O$ (21.4 mL, 286 mmol) was added slowly at ambient temperature and the reaction mixture was stirred for several hours. The solvent was evaporated in vacuo to give a foam which was dissolved in $CH_2Cl_2$ and purified by column chromatography using $CH_2Cl_2$—EtOAc, 25: 75, $CH_2Cl_2$—EtOAc—MeOH, 25:75:2, then $CH_2Cl_2$—EtOAc—MeOH, 25:75:4, to provide the title compound as a foam (30.33 g) which was contaminated with $POPh_3$ (1.0 mol-eq). A small amount of product was purified by column chromatography and characterized.

$^1H$ NMR (DMSO-$d_6$): δ 8.10 (s, 1H), 7.3–7.6 (m, 10H), 6.91 (d, 1H, $J_{a,b}$=7.6 Hz), 6.49 (d, 1H, $J_{a,b}$=7.6 Hz), 5.91 (d, 1H, $J_{1',2'}$=4.9 Hz), 5.27 (d, 1H), 4.42 (m, 2H), 4.08 (m, 2H), 3.99 (m, 1H), 3.6–3.9 (m, 4H), 2.75 (m, 1H), 1.10 (d, 6H), 0.96 (s, 9H). $^{13}C$ NMR ($CDCl_3$): δ 179.6, 155.7, 148.2, 147.9, 138.1, 137.2, 135.4, 135.3, 132.6, 132.4, 129.8, 127.7, 127.5, 121.0, 86.4, 84.8, 83.2, 72.6, 69.9, 69.1, 63.4, 36.0, 26.8, 19.1, 18.9. HRMS (FAB) calcd for $C_{33}H_{42}N_6O_7Si+H^+$: 663.2963; found: 663.2971. Anal. Calcd for $C_{33}H_{42}N_6O_7Si$: C, 59.80; H, 6.39; N, 12.68; found: C, 59.59, H, 6.31, N, 12.5.

Example 18

5'-O-t-Butyldiphenylsilyl-N2-isobutyryl-2'-O-(dimethylaminooxyethyl)guanosine

5'-O-t-Butyldiphenylsilyl-N2-isobutyryl-2'-O-(methyleneimino-N-oxyethyl)guanosine (28.45 g, 30.2 mmol, corrected) containing $POPh_3$ (1.0 mol-eq) as impurity and pyridinium p-toluene sulfonate (75.4 g, 300 mmol) were dissolved in anhydrous MeOH (300 mL), the reaction was cooled to 5° C., and $NaCNBH_3$ (1.90 g, 30 mmol) was slowly added. After several minutes additional $NaCNBH_3$ (1.90 g, 30 mmol) was slowly added at 5° C., and the reaction mixture was allowed to warm to ambient temperature. After 1.5 hours at ambient temperature the solvent was evaporated in vacuo at 26° C. to a volume of 150 mL, EtOAc (750 mL) was added followed by addition of water (100 mL). The mixture was shaken, brine (100 mL) was added, the organic was separated, and the water-brine wash was repeated. The first two aqueous washes were combined, extracted with EtOAc twice (2×200 mL), then all of the organic extracts were combined and washed with brine. The solvent was dried with $MgSO_4$ and evaporated in vacuo to give the monomethylaminooxy derivative as a foam (33.97 g). The reductive amination was repeated as illustrated above in Example 7, and work-up gave a crude product which was purified by column chromatography using $CH_2Cl_2$—EtOAc—MeOH, 25:75:1, $CH_2Cl_2$—EtOAc—MeOH, 25:75:3, $CH_2Cl_2$—EtOAc—MeOH, 25:75:5, $CH_2Cl_2$—EtOAc—MeOH, 25:75:8, to give the title compound as a foam (19.42 g, 95%).

$^1H$ NMR (DMSO-$d_6$): δ 8.14 (s, 1H), 7.3–7.7 (m, 10H), 5.95 (d, 1H, $J_{1',2'}$=5.4 Hz), 5.30 (d, 1H), 4.43 (m, 2H), 4.04 (m, 1H), 3.66 (m, 2H), 3.5–3.9 (m, 4H), 2.75 (m, 1H), 2.38 (s, 6H), 1.14 (d, 6H), 1.01 (s, 9H). $^{13}C$ NMR ($CDCl_3$): δ 179.5, 155.8, 148.4, 148.0, 137.2, 135.6, 135.4, 132.8, 132.6, 129.9, 127.8, 121.3, 86.6, 85.1, 83.3, 70.7, 70.0, 69.4, 63.6, 47.5, 36.1, 26.9, 19.2, 19.0. HRMS (FAB) calcd for $C_{34}H_{46}N_6O_7Si+H^+$: 679.3276; found: 679.3277. Anal. Calcd for $C_{34}H_{46}N_6O_7Si$: C, 60.16; H, 6.83; N, 12.38; found: C, 59.78, H, 6.67, N, 12.23.

Example 19

N2-Isobutyryl-2-O-(dimethylaminooxyethyl) guanosine

Triethylamine trihydrofluoride (46.4 mL, 284 mmol) and $NEt_3$ (19.8 mL, 142 mmol) were added to anhydrous THF (284 mL) to give a suspension to which 5'-O-t-butyldiphenylsilyl-N2-isobutyryl-2'-O-(dimethylaminooxyethyl)guanosine (19.31 g, 28.44 mmol) was added. After stirring for 12 hours the solvent was evaporated in vacuo to give an oil which was dissolved in MeOH and adsorbed unto silica. The product was purified by column chromatography using $CH_2Cl_2$—MeOH, 85:15, to give the title compound as a solid which was contaminated with $NEt_3(HF)_3$.

$^1H$ NMR (DMSO-$d_6$): δ 8.28 (s, 1H), 5.88 (d, 1H, $J_{1',2'}$=6.7 Hz), 5.19 (m, 1H), 5.09 (m, 1H), 4.40 (m, 1H), 4.27 (m, 1H), 3.93 (m, 1H), 3.3–3.6 (m, 6H), 2.34 (s, 6H), 1.09 (d, 6H). $^{13}C$ NMR ($CD_3OD$): δ 181.7, 157.5, 150.5, 150.0, 139.8, 121.2, 87.8, 87.1, 84.3, 71.6, 70.8, 70.7, 62.5, 47.8, 36.9, 19.4 HRMS (FAB) calcd for $C_{18}H_{28}N_6O_7+Na^+$: 463.1917; found: 463.1901.

Example 20

5'-O-(4,4'-dimethoxytrityl)-N2-isobutyryl-2'-O-(dimethylaminooxyethyl)guanosine

To N2-isobutyryl-2-O-(dimethylaminooxyethyl) guanosine (42.63 g, 27.44 mmol) and dimethylaminopyridine (168 mg, 1.37 mmol) dissolved in anhydrous pyridine (274 mL) was added DMT-Cl (9.30 g, 27.44 mmol). After several hours additional DMT-Cl (9.30 g, 27.44 mmol) was added. After several more hours MeOH (22 mL, 543 mmol) was added, and the reaction mixture was stirred for 30 minute. The solvent was evaporated in vacuo to give an oil which was dissolved in EtOAc (550 mL). The resulting suspension was washed with a mixture of $H_2O$ (50 mL) and brine (25 mL) twice, then with brine (50 mL). $NEt_3$ (5 mL) was added, the organic phase was dried with $MgSO_4$ and the solvent was evaporated in vacuo to give a foam. The foam was purified by column chromatography (silica pretreated with 1% $NEt_3$) using $CH_2Cl_2$—EtOAc—MeOH—$NEt_3$, 75:25:10:1, to afford the title compound as a foam (16.3 g, 80%).

$^1H$ NMR ($CDCl_3$): δ 7.87 (s, 1H), 6.7–7.5 (m, 14H), 5.94 (d, 1H, $J_{1',2'}$=5.9 Hz), 4.71 (m, 1H), 4.49 (m, 1H), 4.22 (m, 1H), 3.80 (m, 2H), 3.76 (s, 3H), 3.75 (s, 3H), 3.48 (m, 1H), 3.25 (m, 1H), 2.56 (s, 6H), 2.18 (m, 1H), 0.97 (d, 3H), 0.88 (d, 3H). $^{13}C$ NMR ($CDCl_3$) 178.8, 158.5, 156.0, 148.3, 147.7, 144.7, 138.3, 135.8, 135.5, 129.9, 127.9, 126.9, 121.8, 113.1, 86.6, 86.2, 84.2, 81.8, 70.5, 69.9, 69.5, 63.5, 55.1, 47.3, 35.7, 18.5. HRMS (FAB) calcd for $C_{39}H_{46}N_6O_9+Na^+$: 765.3224; found 765.3215.

Example 21

5'-O-(4,4'-dimethoxytrityl)-N2-isobutyryl-2'-O-(dimethyl-aminooxyethyl)guanosine-3'-(2-cyanoethyl-N,N-diisopropylphosphoramidite)

To a solution of 5'-O-(4,4'-dimethoxytrityl)-N2-isobutyryl-2'-O-(dimethylaminooxyethyl)guanosine (5.049 g, 6.80 mmol) dissolved in $CH_2Cl_2$ (70 mL) was added diisopropylamine tetrazolide (590 mg, 3.45 mmol) and 2-cyanoethyl-N,N,N',N'-tetraisopropylphosphorodiamidite (3.60 mL, 11.3 mmol). After 2 hours at ambient temperature additional 2-cyanoethyl-N,N,N',N'-tetraisopropylphosphorodiamidite (3.60 mL, 11.3 mmol) was added and the solution was stirred for several hours after which EtOAc (700 mL) and $NEt_3$ (7 mL) were added. The organic phase was washed with saturated $NaHCO_3$ thrice (140 mL, 2×70 mL), then with brine twice (2×70 mL), and then the organic phase was dried with $MgSO_4$. The solvent was evaporated in vacuo at 27° C. to give an oil which was dissolved in $CH_2Cl_2$ (68 mL) and $NEt_3$ (0.68 mL). Hexanes were slowly added to the rapidly stirred solution via addition funnel. After addition of about 140 mL of hexanes the stirred solution became turbid and further slow addition gave an oil. Hexanes were added while stirring to a volume of 1700 mL to give a slightly turbid solution with an oil at the bottom of the flask. After standing for several hours the mixture gave a clear supernatant and an oil. The supernatant was decanted, the oil was washed with hexanes thrice, the washes were decanted, and the product was dried in vacuo (0.1 torr) to give a foam (8.48 g). The precipitation procedure was repeated to afford the title compound as a non-hygroscopic foam (6.018 g, 93%) which contained 6 mol % of the hydrolyzed reagent by $^{31}P$ NMR.

$^{31}P$ NMR ($CDCl_3$): δ 150.7, 150.2. HRMS (FAB) calcd for $C_{48}H_{63}N_8O_{10}P+Na^+$: 965.4302; found: 965.4341.

Example 22

5'-O-t-Butyldiphenylsilyl-2'-O-(methoxycarbonylmethylene)-2,6-diaminopurin-9-yl-riboside 2'-O-(Methoxycarbonylmethylene)-2,6-diaminopurin-9-yl-riboside is treated with t-butylchlorodiphenylsilane as per the procedure of Example 13 to give the title compound.

Example 23

5'-O-t-Butyldiphenylsilyl-2-O-(hydroxyethyl)-2,6-diaminopurin-9-yl-riboside

5'-O-t-Butyldiphenylsilyl-2'-O-(methoxycarbonylmethylene)-2,6-diaminopurin-9-yl-riboside is treated with sodium borohydride as per the procedure of Example 14 to give the title compound.

Example 24

5'-O-t-Butyldiphenylsilyl-2'-O-(methoxyethyl)-2,6-diaminopurin-9-yl-riboside

5'-O-t-Butyldiphenylsilyl-2'-O-(hydroxyethyl)-2,6-diaminopurin-9-yl-riboside is treated with methyliodide following a known literature procedure (Williamson reaction, see: March, J., *Advanced organic Chemistry*, 1992, Wiley Interscience, New York, 1992; fourth edition pp. 386–387) to give the title compound.

Example 25

N2-Isobutyryl-2-O-(methoxyethyl)guanosine

5'-O-t-Butyldiphenylsilyl-2'-O-(methoxyethyl)-2,6-diaminopurin-9-yl-riboside is treated with TBAF as per the procedure of Example 8 to remove the 5'-protecting group. The deprotected compound is treated with adenosine deaminase followed by trimethylsilyl chloride, as disclosed in International Patent Application PCT/US93/06807, filed Jul. 20, 1993, entitled "Novel 2'-O-Alkyl Nucleosides and Phosphoramidites Processes for the Preparation and Uses Thereof," which is commonly assigned and is incorporated herein by reference, to give the title compound.

Example 26

5'-O-t-Butyldiphenylsilyl-2-O-(methoxyethyl) adenosine

5'-O-t-Butyldiphenylsilyl-2'-O-(hydroxyethyl)adenosine is treated with methyliodide as per the procedure of Example 24 to give the title compound.

Example 27

N6-Benzoyl-2'-O-(methoxyethyl)-adenosine

5'-O-t-Butyldiphenylsilyl-2'-O-(methoxyethyl)adenosine is treated with TBAF as per the procedure of Example 8 and subsequently treated with benzoyl chloride as per the procedure of Example 4 to give the title compound.

Example 28

3-Benzyloxymethyl-5-methyluridine 25

A solution of 5-methyluridine (51.6, 200 mmol) in DMF (100 mL) was treated with sodium hydride (60% oil, 9.9 g, 248 mmol). After 1 hour at room temperature, benzylchloromethyl ether (34.4 g, 220 mmol) was added dropwise and the reaction mixture heated to 35° C. for 4 hours. The reaction mixture was cooled, quenched with MeOH (5 mL), filtered and concentrated in vacuo. The resultant gum was partitioned between EtOAc/saturated NaCl, separated and dried. The organic phase was concentrated and the title compound collected in crystalline form.

$^1H$ NMR (DMSO-$d_6$) δ 5.83 (d, 1H, $C_{1'}$-H)

Example 29

3-Benzyloxymethyl-2-O-(methoxycarbonylmethylene)-5-methyluridine

3-Benzyloxymethyl-5-methyluridine (9.70 g, 25.6 mmol) was dissolved in anhydrous DMF (250 mL), the reaction mixture was cooled to 5° C., NaH (60% oil dispersion) (1.025 g, 25.6 mmol) was added, the reaction mixture was allowed to warm to ambient temperature, and it was stirred for 1 hour. The suspension was cooled to −40° C. in an $CH_3CN$—$CO_{2(s)}$ bath and methyl 2-bromoacetate (2.36 mL, 25.6 mmol) was added slowly. The reaction mixture was allowed to slowly warm to ambient temperature over 1 hour, then stirred for 16 hours at ambient temperature. MeOH (10 mL) was added followed by addition of glacial AcOH (5 mL), and the reaction mixture was stirred for 5 minutes. The solvent was evaporated in vacuo to give an oil which was dissolved in EtOAc (500 mL), and the organic phase was washed with water (3×50 mL) and brine (50 mL). After drying the organic phase with $Na_2SO_4$, the solvent was evaporated in vacuo to give an oil which was dissolved in 2M $NEt_3$ in anhydrous MeOH (64 mL). After stirring at ambient temperature for 1 hour the solvent was evaporated in vacuo to give an oil which was purified by column chromatography using $CH_2Cl_2$—MeOH, 95:5, to give 2.99 g (26%) of the title compound as a hygroscopic white foam. A second fraction gave 5.57 g (48%) of the title compound with minor impurities (~5%) as a foam.

$^1H$ NMR ($CDCl_3$): 7.63 (s, 1H), 7.30 (m, 5H), 5.72 (d, 1H, $J_{1',2'}$=3.0 Hz), 5.47 (s, 2H), 4.69 (s, 2H), 4.39 (q $_{a,b}$ 2H, $J_{a,b}$=17.6 Hz), 4.2–4.0 (m, 3H), 3.8–3.6 (m, 2H), 3.74 (s, 3H), 1.89 (s, 3H). $^{13}$C NMR (CDCl$_3$) 171.7, 163.3, 150.8, 137.6, 135.9, 128.1, 127.5, 127.4, 109.7, 90.3, 84.5, 83.5, 72.1, 70.3, 68.2, 67.9, 60.9, 52.2, 12.9. HRMS (FAB) calcd for C$_{21}$H$_{26}$N$_2$O$_9$+Na$^+$: 473.1536; found: 473.1549. 2D-$^1$H NMR (TOCSY) confirmed 2'-O-alkylation.

Example 30

5'-O-t-Butyldiphenylsilyl-3-benzyloxymethyl-2'-O-(methoxycarbonylmethylene)-5-methyluridine 3-Benzyloxymethyl-2'-O-(methoxycarbonylmethylene)-5-methyluridine is treated with t-butyldiphenylsilyl chloride as per the procedure of Example 2 above to give the title compound.

Example 31

5'-O-t-Butyldiphenylsilyl-3-benzyloxymethyl-2'-O-(hydroxyethyl)-5-methyluridine

5'-O-t-Butyldiphenylsilyl-3-benzyloxymethyl-2'-O-(methoxycarbonylmethylene)-5-methyluridine is treated with NaBH$_4$ as per the procedure of Example 3 above to give the title compound.

Example 32

5'-O-t-Butyldiphenylsilyl-3-benzyloxymethyl-2'-O-(methoxyethyl)-5-methyluridine

5'-O-t-Butyldiphenylsilyl-3-benzyloxymethyl-2'-O-(hydroxyethyl)-5-methyluridine is treated with methyl iodide following a known literature procedure (Williamson reaction, March, J., *Advanced Organic Chemistry*, 1992, Wiley Interscience, New York, 4$^{th}$ ed., pp. 386–387), to give the title compound.

Example 33

5'-O-t-Butyldiphenylsilyl-2'-O-(methoxyethyl)-5-methyluridine

5'-O-t-Butyldiphenylsilyl-3-benzyloxymethyl-2'-O-(methoxyethyl)-5-methyluridine is dissolved in anhydrous MeOH and is added to a pressure bottle containing 10% Pd on carbon under an argon atmosphere. The vessel is pressurized with hydrogen gas to 30 psi and shaken for 16 hours. The mixture is filtered through a celite pad and the solvent is evaporated in vacuo. The residue is dissolved in 1M NEt$_3$ in anhydrous MeOH and the solution is heated at reflux temperature for 2 hours. The solvent is evaporated in vacuo to give the title compound.

Example 34

2'-O-(methoxyethyl)-5-methyluridine

5'-O-t-Butyldiphenylsilyl-2'-O-(methoxyethyl)-5-methyluridine is treated with TBAF as per the procedure of Example 8 above to give the title compound.

Example 35

2'-O-(Methoxycarbonylmethylene)-5-methyluridine

3-Benzyloxymethyl-2'-O-(methoxycarbonylmethylene)-5-methyluridine (2.99 g, 6.64 mmol) was dissolved in anhydrous MeOH (80 mL) and added to a pressure bottle containing 10% Pd on carbon (750 mg) under an argon atmosphere. The vessel was pressurized with hydrogen gas to 30 psi and shaken for 16 hours. The mixture was filtered through a celite pad and the solvent was evaporated in vacuo to give an oil. The oil was dissolved in 1M NEt$_3$ in anhydrous MeOH and the solution was heated at reflux temperature for 2 hours. The solvent was evaporated in vacuo to give 2.735 g (95%) of title compound as a white solid.

$^1$H NMR (DMSO-d$_6$): 11.4 (br s, 1H), 7.75 (s, 1H), 5.92 (d, 1H, $J_{1',2'}$=5.2 Hz), 5.19 (m, 2H), 4.24 (m, 2H), 3.87 (m, 1H), 3.63 (s, 3H), 1.78 (s, 3H). $^{13}$C NMR (pyridine-d$_5$): 171.3, 165.0, 152.1, 136.7, 110.2, 88.1, 85.9, 84.1, 69.6, 68.0, 61.0, 51.7, 12.7. LRMS (ES): m/z 352.8 (M+Na)$^+$.

Example 36

2'-O-(hydroxyethyl)-5-methyluridine

2'-O-(Methoxycarbonylmethylene)-5-methyluridine is prepared via photochemical reductive deoxygenation of the 2'-O-ester function with trichlorosilane following a literature procedure. Baldwin et al., *J. Org. Chem.*, 1975, 40, 3885–3887.

Example 37

5'-O-t-Butyldiphenylsilyl-2'-O-(hydroxyethyl)-5-methyluridine

5'-O-t-Butyldiphenylsilyl-3-benzyloxymethyl-2'-O-(hydroxyethyl)-5-methyluridine prepared in Example 31 above is hydrogenated using 10% Pd on carbon as per the procedure of Example 35 above to give the title compound.

Example 38

2'-O-([2-phthalimidoxy)ethyl]-5'-t-butyldiphenylsilyl-5-methyluridine

5'-O-t-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. The resultant residue was placed on a flash column and eluted with ethyl acetate:hexane (60:40), to obtain the title compound as a white foam (21.819, 86%). Rf 0.56 (ethyl acetate:hexane, 60:40). MS (FAB$^-$)m/e 684 (M–H$^+$)

Example 40

5'-O-t-butyldiphenylsilyl-2'-O-[(2-formadoximinooxy) ethyl]-5-methyluridine

2'-O-([2-Phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at –10° C. to 0° C. After 1 hr the mixture was filtered, the filtrate was washed with ice cold CH$_2$Cl$_2$ and the combined organic phase was washed with water, brine and dried over anhydrous Na$_2$SO$_4$. The solution concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent removed under vacuum; residue chromatographed to give the title compound as white foam (1.95, 78%). Rf 0.32 (5% MeOH in $CH_2Cl_2$). MS (Electrospray$^-$) m/e 566 (M–H$^\ominus$)

Example 40

5'-O-t-Butyldiphenylsilyl-2'-O-[N,N-dimethylaminooxyethyl]-5-methyluridine

5'-O-t-Butyldiphenylsilyl-2'-O-[(2-formadoximinooxy)-ethyl]-5-methyluridine (1.77 g, 3.12mmol) was dissolved in a solution of 1M pyridinium p-toluenesulfonate (PPTS) in dry MeOH (30.6 mL). Sodiumcyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction was monitored by TLC (5% MeOH in $CH_2Cl_2$). Aqueous $NaHCO_3$ solution (5%, 10 mL) was added and extracted with ethyl acetate (2×20 mL). Ethyl acetate phase dried over anhydrous $Na_2SO_4$, evaporated to dryness. Residue dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodiumcyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to give the title compound as a white foam (14.6 g, 80%). Rf 0.35 (5% MeOH in $CH_2Cl_2$). MS (FAB$^\oplus$) m/e 584 (M+H$^\oplus$)

Example 41

2'-O-(Dimethylaminooxyethyl)-5-methyluridine

To a solution of triethylamine trihydrofluoride (3.91 mL, 24.0 mmol) dissolved in dry THF and triethylamine (1.67 mL, 12 mmol, dry, kept over KOH) was added 5'-O-t-butyldiphenylsilyl-2'-O-[N,N-dimethylaminooxyethyl]-5-methyluridine (1.40 g, 2.4 mmol) and the resultant mixture was stirred at room temperature for 24 hrs. The reaction was monitored by TLC (5% MeOH in $CH_2Cl_2$). The solvent was removed under vacuum and the residue placed on a flash column and eluted with 10% MeOH in $CH_2Cl_2$ to give the title compound (766 mg, 92.5%). Rf 0.27 (5% MeOH in $CH_2Cl_2$). MS (FAB$^\oplus$) m/e 346 (M+H$^\oplus$)

Example 42

5'-O-DMT-2'-O-(dimethylaminooxyethyl)-5-methyluridine

2'-O-(Dimethylaminooxyethyl)-5-methyluridine (750 mg, 2.17 mmol) was dried over $P_2O_5$ under high vacuum overnight at 40° C. and then co-evaporated with anhydrous pyridine (20 mL). The residue obtained was dissolved in pyridine (11 mL) under and atmosphere of argon atmosphere. 4-Dimethylaminopyridine (26.5 mg, 2.60 mmol) and 4,4'-dimethoxytrityl chloride (880 mg, 2.60 mmol) was added with stirring until dissolution of all starting material. The pyridine was removed under vacuum and the residue chromatographed using 10% MeOH in $CH_2Cl_2$ (containing a few drops of pyridine) as the eluent to give the title compound (1.13 g, 80%). Rf 0.44 ((10% MeOH in $CH_2Cl_2$). MS (FAB$^\oplus$) m/e 648 (M+H$^\oplus$)

Example 43

5'-O-DMT-2'-O-(2-N,N-dimethylaminooxyethyl)-5-methyluridine-3'-[(2-cyanoethyl)-N,N-diisopropylphosphoramidite]

To 5'-O-DMT-2'-O-(dimethylaminooxyethyl)-5-methyluridine (1.08 g, 1.67 mmol) that was co-evaporated with toluene (20 mL) was added N,N-diisopropylamine tetrazonide (0.29 g, 1.67 mmol) was added and the mixture was dried over $P_2O_5$ under high vacuum overnight at 40° C. The mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under an atmosphere of argon. The progress of the reaction was monitored by TLC (hexane:ethyl acetate 1:1). The solvent was evaporated and the resultant residue was dissolved in ethyl acetate (70 mL) and washed with 5% aqueous $NaHCO_3$ (40 mL). The ethyl acetate layer was dried over anhydrous $Na_2SO_4$ and concentrated. The residue obtained was chromatographed (ethyl acetate as eluent) to give the title compound as a foam (1.04 g, 74.9%). Rf 0.25 (ethyl acetate:hexane, 1:1). $^{31}$P NMR (CDCl$_3$) δ 150.8 ppm; MS (FAB$^\oplus$) m/e 848 (M+H$^\oplus$).

Example 44

5'-O-t-Butyldiphenylsilyl-2'-O-(phthalimido-N-oxyethyl)-5-methyluridine

PPh$_3$ (6.31 g, 24.04 mmol) and N-hydroxyphthalimide (3.92 g, 24.04 mmol) were added to dried 5'-O-t-butyldiphenylsilyl-2'-O-(hydroxyethyl)-5-methyluridine (10.00 g, 18.5 mmol) dissolved in anhydrous THF (185 mL). The reaction mixture was cooled to 5° C. and diethylazodicarboxylate (3.79 mL, 24.04 mmol) was added slowly. The reaction mixture was allowed to warm to ambient temperature and after stirring for 16 h the solvent was evaporated in vacuo to give an oil. The product was dissolved in $CH_2Cl_2$ and purified by column chromatography using hexanes-EtOAc, 30:70 as the eluent, to give the title compound as a white foam (11.69 g, 92%).

$^1$H NMR (DMSO-d$_6$): 11.3 (br s, 1H), 7.8–7.4, (m, 15H), 5.90, (d, 1H, $J_{1',2'}$=6.0 Hz), 5.17, (d, 1H), 4.30, (m, 3H), 4.03, (m, 2H), 3.87, (m, 5H), 1.43, (s, 3H), 1.00, (s, 9H). $^{13}$C NMR (CDCl$_3$): 164.0163.6, 150.5, 135.4, 135.1, 134.8, 134.5, 133.1, 132.3, 129.9, 128.6, 127.8, 127.5, 123.6, 110.9, 87.4, 84.1, 83.0, 77.6, 68.4, 68.2, 62.5, 26.9, 19.3, 11.7. Anal calcd for $C_{36}H_{39}N_3O_9Si$: C, 63.05; H, 5.73; N, 6.13; found: C, 62.87; H, 5.54; N, 5.94.

Example 45

5'-O-t-Butyldiphenylsilyl-2'-O-(piperidinyl-N-oxyethyl)-5-methyluridine

5'-O-t-Butyldiphenylsilyl-2'-O-(phthalimido-N-oxyethyl)-5-methyluridine (686 mg, 1.0 mmol) was dissolved in $CH_2Cl_2$, the reaction mixture was cooled to 5° C., and NHMeNH$_2$ (0.585 mL, 1.10 mmol) was added dropwise. After stirring at 5° C. for 1 h a white precipitate formed which was filtered, washed with cold $CH_2Cl_2$. The combined filtrates were evaporated in vacuo to give a crude residue. The residue was dissolved in anhydrous MeOH (10 mL), 50% aqueous glutaraldehyde (1.00 mL, 5.52 mmol) was added dropwise, and the reaction mixture was stirred at ambient temperature for 12 h. The solvent was evaporated in vacuo to give a crude product which was dissolved in $CH_2Cl_2$ (50 mL). The organic phase was separated and washed with water (3×10 mL), brine, and dried with $Na_2SO_4$. The solvent was evaporated in vacuo to give the oxime as a crude oil which was dissolved in anhydrous MeOH (5 mL). PPTS (1.256 g, 5.0 mmol) was added to the solution with cooling to 5° C. followed by the addition of $NaCNBH_3$ (69 mg, 1.10 mmol). The reaction mixture was allowed to warm to ambient temperature and stirred for 2 h, after which the solvent was evaporated in vacuo at 25° C. to give an oil. The product was dissolved in EtOAc (100 mL), the organic was washed with water (3×20 mL), brine (20 mL) and the solvent was evaporated in vacuo to give the crude product. The crude product was purified by column chromatography using hexane-EtOAc, 30:70 as the eluent, to afford the title compound as a white foam (283 mg, 45%).

$^1$H NMR ($CDCl_3$): 9.2 (br s, 1H), 7.7–7.2 (m, 11 H), 6.06 (d, 1H, J 1', 2'=4.4 Hz), 4.5 (br s, 1H), 4.35 (m, 1H), 4.0–3.6 (m, 8H), 3.3 (m, 2H), 2.4 (m, 2H), 2.0–1.6 (m, 6H), 1.52 (s, 3H), 1.11 (s, 9H). $^{13}$C NMR ($CDCl_3$): 164.1, 150.5, 135.4, 135.1, 132.9, 132.2, 129.9, 130.0, 127.8, 127.5, 111.0, 86.9, 84.5, 83.1, 71.1, 69.8, 68.9, 63.2, 56.7, 26.9, 25.1, 23.2, 19.3, 11.8. HRMS (FAB) calcd for $C_{33}H_{45}N_3O_7Si+Cs^+$: 756.2081; found: 756.2102. Anal calcd for $C_{33}H_{45}N_3O_7Si$: C, 63.54; H, 7.27; N, 6.74; found: C, 63.21; H, 7.15; N, 6.76.

Example 46

Synthesis of Aminooxy Derivatives: Alternative Procedure

The 2'-O-hydroxyethyl compounds (5'-O-t-butyldiphenylsilyl-N6-benzoyl-2'-O-(hydroxyethyl) adenosine, Example 4; 5'-O-t-butyldiphenylsilyl-2'-O-(hydroxyethyl)guanosine, Example 14; and 5'-O-t-butyldiphenylsilyl-3-benzyloxymethyl-2'-O-(hydroxyethyl)-5-methyluridine, Example 31) are converted into their respective 2'-O-$CH_2CH_2$-O-tosylate derivatives by treatment with 1 equivalent of p-toluenesulfonyl chloride-pyridine. The tosylate is subsequently treated with one of several amino-hydroxy compounds that are effective nucleophiles in displacing tosylate to yield a series of oxy-amino compounds. The reaction is facilitated by preforming the anion from the amino alcohol or hydroxylamine derivative by the use of sodium hydride under anhydrous conditions.

BIOLOGICAL PROTOCOLS

Procedure 1

Nuclease Resistance

A. Evaluation of the resistance of modified oligonucleotides to serum and cytoplasmic nucleases.

Oligonucleotides including the modified oligonucleotides of the invention can be assessed for their resistance to serum nucleases by incubation of the oligonucleotides in media containing various concentrations of fetal calf serum or adult human serum. Labeled oligonucleotides are incubated for various times, treated with protease K and then analyzed by gel electrophoresis on 20% polyacrylamide-urea denaturing gels and subsequent autoradiography. Autoradiograms are quantitated by laser densitometry. Based upon the location of the modifications and the known length of the oligonucleotide it is possible to determine the effect on nuclease degradation by the particular modification. For the cytoplasmic nucleases, a HL60 cell line is used. A post-mitochondrial supernatant is prepared by differential centrifugation and the labeled oligonucleotides are incubated in this supernatant for various times. Following the incubation, oligonucleotides are assessed for degradation as outlined above for serum nucleolytic degradation. Autoradiography results are quantitated for comparison of the unmodified and modified oligonucleotides. As a control, unsubstituted phosphodiester oligonucleotide have been found to be 50% degraded within 1 hour, and 100% degraded within 20 hours.

B. Evaluation of the resistance of modified oligonucleotides to specific endo- and exonucleases.

Evaluation of the resistance of natural and modified oligonucleotides to specific nucleases (i.e., endonucleases, 3',5'-exo-, and 5',3'-exonucleases) is done to determine the exact effect of the modifications on degradation. Modified oligonucleotides are incubated in defined reaction buffers specific for various selected nucleases. Following treatment of the products with protease K, urea is added and analysis on 20% polyacrylamide gels containing urea is done. Gel products were visualized by staining using StainsAll (Sigma Chemical Co.). Laser densitometry is used to quantitate the extend of degradation. The effects of the modifications are determined for specific nucleases and compared with the results obtained from the serum and cytoplasmic systems.

| Nuclease resistance of oligonucleotides containing novel 2'-modifications Series I 5' TTT TTT TTT TTT TTT*T*T*T* T 3' | | |
|---|---|---|
| SEQ ID NO: 1 | where T* = 5 methyl, 2'-aminooxyethoxy | 2' AOE |
| SEQ ID NO: 2 | where T* = 5 methyl, 2'-dimethylaminooxyethoxy | 2' DMAOE |

Along with T19 diester and thioate controls, the gel-purified oligonucleotides were 5'-end labeled with $^{32}$P, and run through the standard nuclease assay protocol. PAGE/Phosphorimaging generated images that were quantified for % Intact and % (Intact+(N−1)). The percentages were plotted to generate half-lives ($T_{1/2}$), which are listed in Table 1 below. Included is the half life of the 2'-O-methoxyethyl (MOE) analog (SEQ ID NO 3). This result showed that 2'-dimethylaminooxyethyl (DMAOE) is a highly nuclease resistant modification.

TABLE 1

| $T_m$ values of oligonucleotides bearing 2'-modifications | | | |
|---|---|---|---|
| | 2'-Modification | | |
| | AOE | DMAOE | MOE |
| $T_{1/2}$ of N (min) | 18 | 60 | 100 |
| $T_{1/2}$ of N + (N − 1) (min) | 200 | 85% remaining at 24 hr. | 300 |

Initial assays of the nuclease resistance of oligonucleotides capped with 2'-DMAOE modifications showed better resistance than modification 2'-O-methoxyethyl in an inter-assay comparison (FIG. 13). These studies are intra-assay comparisons among several modifications in two motifs. The first motif is a full phosphodiester backbone, with a cap of 4 modified nucleotides beginning at the 3'-most nucleotide. The second motif is similar, but contains a single phosphorothioate at the 3'-most inter nucleotide linkage.

Series II
5' TTT TTT TTT TTT TTT T*T*T* T* 3'

| SEQ ID NO: 4 | where T* = 5 methyl, 2'-dimethylaminooxyethyl |
| SEQ ID NO: 5 | where T* = 5 methyl, 2'-O-methoxyethyl |
| SEQ ID NO: 6 | where T* = 5 methyl, 2'-O-propyl |

Series III
5' TTT TTT TTT TTT TTT TTT*T 3'

| SEQ ID NO: 7 | where T* = 5 methyl, 2'-dimethylaminooxyethyl |
| SEQ ID NO: 8 | where T* = 5 methyl, 2'-O-methoxyethyl |

Along with a T19 phosphorothioate control, the oligos were gel purified and run through the standard nuclease protocol. From these assays SEQ ID NO: 4 proved to be the next most resistant oligonucleotide. SEQ ID NO: 5 is degraded more readily, and SEQ ID NO: 6 is degraded rather quickly. The gel shows some reaction products at the bottom of the gel, but little n-2 and n-3 of the resistant oligonucleotides. These products appear to be the result of endonucleolytic cleavage by SVPD. This type of activity is always present at a basal rate, but is not usually seen due to the overwhelming predominance of 3' exonuclease activity on most oligonucleotides. However, these oligonucleotides are so extraordinarily resistant to 3'-exonucleases that the endonuclease activity is responsible for a majority of the cleavage events on the full-length oligo. 2'-deoxy phosphodiester products of the endonuclease reactions are then rapidly cleaved to monomers. Two sets of quantitation are done for these reactions. One counts only 3'-exonuclease products, and the other counts products for all reactions. In either case, the half-life of SEQ ID NO: 4 is longer than 24 hours. For SEQ ID NO: 5 the half life of the exonuclease activity is over 24 hours while the other type of Quantitation gives a half-life of about 100 min. The oligonucleotides of the motif containing a single phosphorothioate linkage (SEQ ID NO: 7 and SEQ ID NO: 8) are substrates for the endonuclease activity described above, but no products of 3' exonuclease activity are detected in the time course of this assay.

TABLE 2

Oligonucleotides synthesized with
2'-dimethylaminooxyethyl thymidine (T-2'-DMAOE)

| SEQ ID NO: | Sequence | Mass Exp. | Mass Obs. |
|---|---|---|---|
| 9 | 5'-CTCGTACCT*TTCCGGTCC-3' | 5784.20 | 5784.09 |
| 10 | 5'-T*CCAGGT*GT*CCGCAT*C-3' | 5548.74 | 5549.05 |
| 11 | 5'-GCGT*T*T*T*T*T*T*T*T*GCG-3' | 6208.74 | 6210.52 |
| 12 | 5'-TTTTTTTTTTTTTTT*T*T*T-3' | 6433.45 | 6433.79 |
| 13 | 5'-T*T*T*T*-3' | 1869.96 | 1869.5 |
| 14 | 5'-TTTTTTTTTTTTTTTT*T*T$_s$T*-3' | 6449.45 | 6449.15 |
| 15 | TTTTTTTTTTTTTTTT*T*T*T*-3' | 6433.51 | 6433.19 |
| 16 | 5'-T*T*-3' | 648.49 | 648.4 |

TABLE 3

Oligonucleotides synthesized with
2'-dimethylaminooxyethyl adenosine
(A-2'-DMAOE)

| SEQ ID NO: | Sequence | Mass Exp. | Mass Obs. |
|---|---|---|---|
| 17 | 5'-CTCGTACCA*TTCCGGTCC-3' | 5490.21 | 5490.86 |
| 18 | 5'GGA*CCGGA*A*GGTA*CGA*G-3' | 5824.96 | 5826.61 |
| 19 | 5'-A*CCGA*GGA*GGA*TCA*TGTCGTA*-CGC-3' | 6947.9 | 6947.28 |

TABLE 4

Oligonucleotides synthesized with
2'-O-methyleneiminooxyethyl adenosine

| SEQ ID NO: | Sequence | Mass Exp. | Mass Obs. |
|---|---|---|---|
| 20 | 5'-CTCGTACCA*TTCCGGTCC-3' | 5470.20 | 5472.50 |
| 21 | 5'-A*CCGA*GGA*TCA*TGTCGTA*CGC-3' | 6866.42 | 6865.88 |
| 22 | 5'-GGA*CCGGA*A*GGTA*CGA*G-3' | 5743.12 | 5743.82 |

TABLE 5

Oligonucleotides synthesized with
2'-O-methyleneiminooxyethyl thymidine

| SEQ ID NO: | Sequence | Mass Exp. | Mass Obs. |
|---|---|---|---|
| 23 | 5'-CTCGTACCT*TTCCGGTCC-3' | 5466.21 | 5462.25 |
| 24 | 5'-T*CCAGGT*GT*CCGCAT*C-3' | 5179.44 | 5178.96 |
| 25 | 5'-TTTTTTTTTTTTTTT*T*T*T-3' | 6369.45 | 6367.79 |

TABLE 6

$T_m$ advantage of 2'-DMAOE modification over 2'-deoxy phosphodiesters and phosphorothioates

| SEQ. ID NO: | SEQUENCE | $T_m$ | $\Delta T_m$/mod against RNA Vs. unmodified DNA | $\Delta T_m$/mod against RNA Vs. unmodified deoxy-phosphorothioate |
|---|---|---|---|---|
| 26 | 5'-CTCGTAC-CT*T-TCCGGTCC-3' | 65.44 | 0.24 | 1.04 |
| 27 | 5'-T*CCAGGT*GT*C-CGCAT*C-3' | 67.90 | 1.12 | 2.20 |
| 28 | 5'-GCGT*T*T*T*T*T*T*T*T*GCG-3' | 62.90 | 1.46 | 2.36 |

$\Delta T_m$ is based on reported literature values for DNA and phosphorothioate oligonucleotides.

What is claimed is:

1. A method for the selective alkylation of the 2' position of 2',3'-dihydroxy sugar moiety of a nucleoside comprising the steps of
   (a) dissolving said nucleoside in at least one aprotic solvent to form a solution;
   (b) cooling said solution to a temperature of from about 5° C. to about minus 50° C.;
   (c) treating said cooled solution with a base to give a mixture;
   (d) warming said mixture to a temperature of from about minus 30° C. to about 35° C.;
   (e) cooling said mixture of step (d) to a temperature of from about 5° C. to about minus 50° C.; and
   (f) reacting said cooled mixture of step (e) with a reactive ester to effect said alkylation.

2. The method of claim 1 wherein said aprotic solvent is selected from the group consisting of dimethylformamide, dimethylsulfoxide, dimethylacetamide, acetonitrile hexamethylphosphoramide and mixtures thereof.

3. The method of claim 1 wherein said solvent is at least two of dimethylformamide, dimethylsulfoxide, dimethylacetamide, acetoinitrile and hexamethylphosphoramide.

4. The method of claim 1 wherein said reactive ester is an alkyl haloalkylate.

5. The method of claim 4 wherein said reactive ester is an alkyl bromoalkylate.

6. The method of claim 5 wherein said reactive ester is methyl bromoacetate.

7. The method of claim 1 wherein said base is 1,5-diazabicyclo[4.3.0]non-5-ene, 1,4-diazabicyclo[2.2.2]octane or 1,8-diazabicyclo[5.4.0]undec-7-ene.

8. The method of claim 1 wherein said base is a metal hydride, a metal hydroxide or a metal carbonate.

9. The method of claim 8 wherein said base is sodium hydride, potassium hydride, lithium hydride, sodium hydroxide, potassium hydroxide, lithium hydroxide, sodium carbonate, potassium carbonate or cesium carbonate.

* * * * *

UNITED STATES PATENT AND TRADEMARK OFFICE
CERTIFICATE OF CORRECTION

PATENT NO. : 6,403,779 B1
DATED : June 11, 2002
INVENTOR(S) : Kawasaki et al.

It is certified that error appears in the above-identified patent and that said Letters Patent is hereby corrected as shown below:

Column 7,
Line 7, please delete "-40°°C.)" and insert therefor -- 40°C.) --;

Column 9,
Lines 53 & 54, please delete "30°°C. to about 35°°C.," and insert therefor
-- 30°C. to about 35°C., --;
Line 54, please delete "30°°" and insert therefor -- 30° --;
Lines 54 & 55, please delete "40°°C. to about minus 50°°C." and insert therefor
-- 40° C. to about minus 50°C. --;

Column 11,
Line 23, please delete "-50°°C.," and insert therefor -- -50°C., --;
Line 27, please delete "-50°°C.," and insert therefor -- -50°C., --;

Column 24,
Line 57, please delete "Example 40" and insert therefor -- Example 39 --;

Signed and Sealed this

Tenth Day of December, 2002

JAMES E. ROGAN
*Director of the United States Patent and Trademark Office*